(12) United States Patent
McLachlan

(10) Patent No.: US 10,316,053 B2
(45) Date of Patent: Jun. 11, 2019

(54) FLAVONOID COMPOUNDS AND USES THEREOF

(71) Applicant: ARMARON BIO PTY LTD, East Melbourne, Victoria (AU)

(72) Inventor: Grant McLachlan, Melbourne (AU)

(73) Assignee: ARMARON BIO PTY LTD, Victoria (AU)

( * ) Notice: Subject to any disclaimer, the term of this patent is extended or adjusted under 35 U.S.C. 154(b) by 0 days.

(21) Appl. No.: 14/435,164

(22) PCT Filed: Oct. 11, 2013

(86) PCT No.: PCT/AU2013/001175
§ 371 (c)(1),
(2) Date: Apr. 12, 2015

(87) PCT Pub. No.: WO2014/056038
PCT Pub. Date: Apr. 17, 2014

(65) Prior Publication Data
US 2015/0259373 A1 Sep. 17, 2015

(30) Foreign Application Priority Data

Oct. 11, 2012 (AU) .............................. 2012904444

(51) Int. Cl.
| | | |
|---|---|---|
| C07D 311/30 | (2006.01) | |
| C07H 15/26 | (2006.01) | |
| C07H 17/07 | (2006.01) | |
| A61K 31/353 | (2006.01) | |
| A61K 31/7048 | (2006.01) | |

(52) U.S. Cl.
CPC ........... *C07H 15/26* (2013.01); *A61K 31/353* (2013.01); *A61K 31/7048* (2013.01); *C07D 311/30* (2013.01); *C07H 17/07* (2013.01)

(58) Field of Classification Search
None
See application file for complete search history.

(56) References Cited

U.S. PATENT DOCUMENTS

| 7,863,323 | B1 * | 1/2011 | Williams ............. C07D 311/62 514/456 |
| 8,017,649 | B2 | 9/2011 | Jarrott et al. |
| 2002/0147353 | A1 | 10/2002 | Van Der Vijgh et al. |
| 2011/0053874 | A1 | 3/2011 | Esperester et al. |

FOREIGN PATENT DOCUMENTS

| CN | 101244057 A | 8/2008 |
| CN | 102617672 A | 8/2012 |
| CN | 102631362 A | 8/2012 |
| CN | 102697768 A | 10/2012 |
| JP | 2003019867 A | 1/2003 |
| JP | 2007230145 A | 9/2007 |
| JP | 2010053067 A | 3/2010 |
| JP | 2012044944 A | 3/2012 |
| WO | 2001003681 A2 | 1/2001 |
| WO | WO 2001/021608 A2 | 3/2001 |
| WO | 2003035900 A1 | 5/2003 |
| WO | 2006030322 A2 | 3/2006 |
| WO | 2006094357 A1 | 9/2006 |
| WO | WO 2006/094357 A1 | 9/2006 |
| WO | 2008011538 A2 | 1/2008 |
| WO | WO 2008/011538 A2 | 1/2008 |
| WO | 2010129138 A2 | 11/2010 |
| WO | WO 2013/020184 A1 | 2/2013 |

OTHER PUBLICATIONS

Ettmayer, P. et al., Journal of Medicinal Chemistry, "Lessons learned from Marketed and Investigational Prodrugs", 2004, vol. 47, No. 10, pp. 2393-2404.*
Stella, V. J. et al., Expert Opinion, "Prodrugs as therapeutics", 2004, vol. 14, No. 3, pp. 277-280.*
Testa, B., Biochemical Pharmacology, "Prodrug research: futile or fertile?", 2004, vol.*
Wolff, M. E., Burger's Medicinal Chemistry and Drug Discovery, Fifth Edition, vol. 1: Principles and Practice, 1995, pp. 975-977.*
Biasutto, L. et al., J. Med. Chem., "Ester-Based Precursors to Increase the Bioavailability of Quercetin", 2007, 50, pp. 241-253 (Year: 2007).*
Cheng Xue Qin et al: "Understanding the Cardioprotective Effects of Flavonols: Discovery of Relaxant Flavonols without Antioxidant Activity", Journal of Medicinal Chemistry, vol. 51, No. 6, Mar. 1, 2008 (Mar. 1, 2008 ), pp. 1874-1884.

(Continued)

*Primary Examiner* — Layla D Berry
*Assistant Examiner* — Bahar Craigo
(74) *Attorney, Agent, or Firm* — Banner & Witcoff, Ltd.

(57) ABSTRACT

The present disclosure provides a compound of the following formula, racemates, enantiomers, prodrugs and salts thereof:

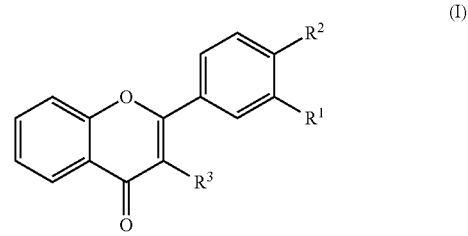

(I)

Also provided is the use of these compounds for the treatment of ischemia and reperfusion injuries. Further applications include the treatment of diseases caused by cell apoptosis and/or cell necrosis.

1 Claim, 3 Drawing Sheets

(56) References Cited

OTHER PUBLICATIONS

CAS Registry No. 1360535-03-0, Entered STN Mar. 8, 2012.
CAS Registry No. 1246650-40-7, Entered STN Oct. 20, 2010.
CAS Registry No. 1203316-35-1, Entered STN Jan. 24, 2010.
CAS Registry No. 1017495-84-9, Entered STN Apr. 27, 2008.
CAS Registry No. 951921-38-3, Entered STN Oct. 30, 2007.
CAS Registry No. 831240-79-0, Entered STN Feb. 15, 2005.
CAS Registry No. 819835-19-3, Entered STN Jan. 25, 2005.
CAS Registry No. 819830-02-9, Entered STN Jan. 25, 2005.
CAS Registry No. 742656-25-3, Entered STN Sep. 10, 2004.
CAS Registry No. 1345720-42-4.
CAS Registry No. 1345720-44-6.
CAS Registry No. 4143-62-8.
CAS Registry No. 1345720-40-2.
CAS Registry No. 6889-80-1.
Gohil V. M. et al. Nutrient-sensitized screening for drugs that shift energy metabolism from mitochondrial respiration glycolysis Nature Biotechnology (2010) 28(3) pp. 249-255 & CAS Registry Nos. 4143-62-8 and 6889-80-1.
Wu, B. et al. Evaluation of 3,3',4'-Trihydroxyflavone and 3,6,4'-Trihydroxyflavone (4'-O-Glucuronidation) as the in Vitro Functional Markers for Hepatic UGT1A1, Molecular Pharmaceutics (2011), 8(6), pp. 2379-2389 & CAS Registry Nos. 1345720-40-2, 1345720-42-4 and 1345720-44-6.
Picq, M. et al Selective inhibition of separated forms of cyclic nucleotide phosphodiesterase from rat heart by some pentasubstituted quercetin analogs. Biochem Pharmacol, (1982), 31, pp. 2777-2782.
Rubio, S. et al. Acetyl derivative of quercetin 3-methyl ether-induced cell death in human leukemia cells is amplified by the inhibition of ERK. Carcinogenesis, (2007), 28, pp. 2105-2113.
Peng, Y. et al. Preparation and prodrug studies of quercetin pentabenzensulfonate. Yakugaku Zasshi, (2008), 128, pp. 1845-1849.
International New Zealand Examination Report dated Jun. 18, 2015.
International Search Report issued in corresponding International Application PCT/AU2013/001175 dated Feb. 12, 2014.
Bross et al., "New fluorescent compounds for plastic scintillator applications," Nuclear Instruments and Methods in Physics Research, A325, 168-75, 1993.
CAS Registry No. 1017495-84-9, 2 pages, 2014.
CAS Registry No. 1203316-35-1, 2 pages, 2014.
CAS Registry No. 1246650-40-7, 2 pages, 2014.
CAS Registry No. 742656-25-3, 2 pages, 2014.
CAS Registry No. 819835-19-3, 2 pages, 2014.
CAS Registry No. 831240-79-0, 2 pages, 2014.
CAS Registry No. 951921-38-3, 2 pages, 2014.
Chan et al., "Flavonoid Dimers as Bivalent Modulators for P-Glycoprotein-Based Multidrug Resistance: Structure-Activity Relationships," ChemMedChem 4, 594-614, 2009.
De Celle et al., "Sustained protective effects of 7-monohydroxyethylrutoside in an in vivo model of cardiac ischemia-reperfusion," European Journal of Pharmacology 494, 205-12, 2004.
Jerzmanowska & Michalska, "Syntheses of Polyhydrozyflavone Glucosides," Chemistry and Industry 1318-19, 1957.
Jung et al., "Neuroprotective Effects of Quercetin 3-O-Methyl Ether, Quercetin and (±)-Dihydroquercetin in a Rat Model of Transient Focal Cerebral Ischemia," Bull. Korean Chem. Soc. 33, 2443-46, 2012.
Li et al., "Synthesis of a library of glycosylated flavonols," Tetrahedron Letters 49, 7243-45, 2008.
Liu et al., "Hyperoside protects cortical neurons from oxygen-glucose deprivation-reperfusion induced injury via nitric oxide signal pathway," Brain Research 1469, 164-73, 2012.
Qin et al., "Antioxidant Activity Contributes to Flavonol Cardioprotection During Reperfusion of Rat Hearts," Free Radical Biology & Medicine doi: 10/1016/j.freeradiobiomed.2011.07.0003, 8 pages, 2011.
Williams et al., "Water soluble flavonol prodrugs that protect against ischaemia-reperfusion injury in rat hindlimb and sheep heart," Med. Chem. Commun. 2, 321-24, 2011.
Wymann et al., "Selective Alkylations of Certain Phenolic and Enolic Functions with Lithium Carbonate/Alkyl Halide," Synthetic Communications 18, 1379-84, 1988.
Yin et al., "Protective Effect of Astragaloside on Focal Cerebral Ischemia/Reperfusion Injury in Rats," American Journal of Chinese Medicine 38, 517-27, 2010.
Zhang et al., "Isorhamnetin protects rat ventricular myocytes from ischemia and reperfusion injury," Experimental and Toxicologic Pathology 63, 33-38, 2011.

\* cited by examiner

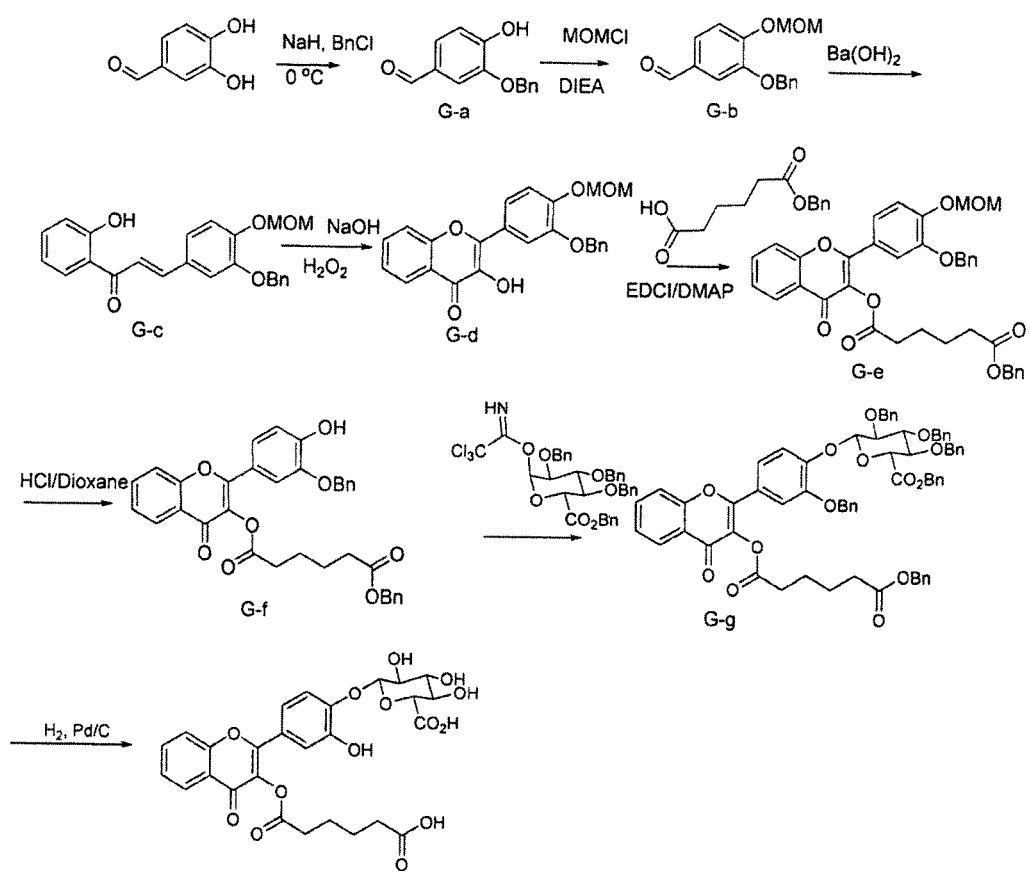
Figure 1: Synthesis of glucuronide 1 (18)

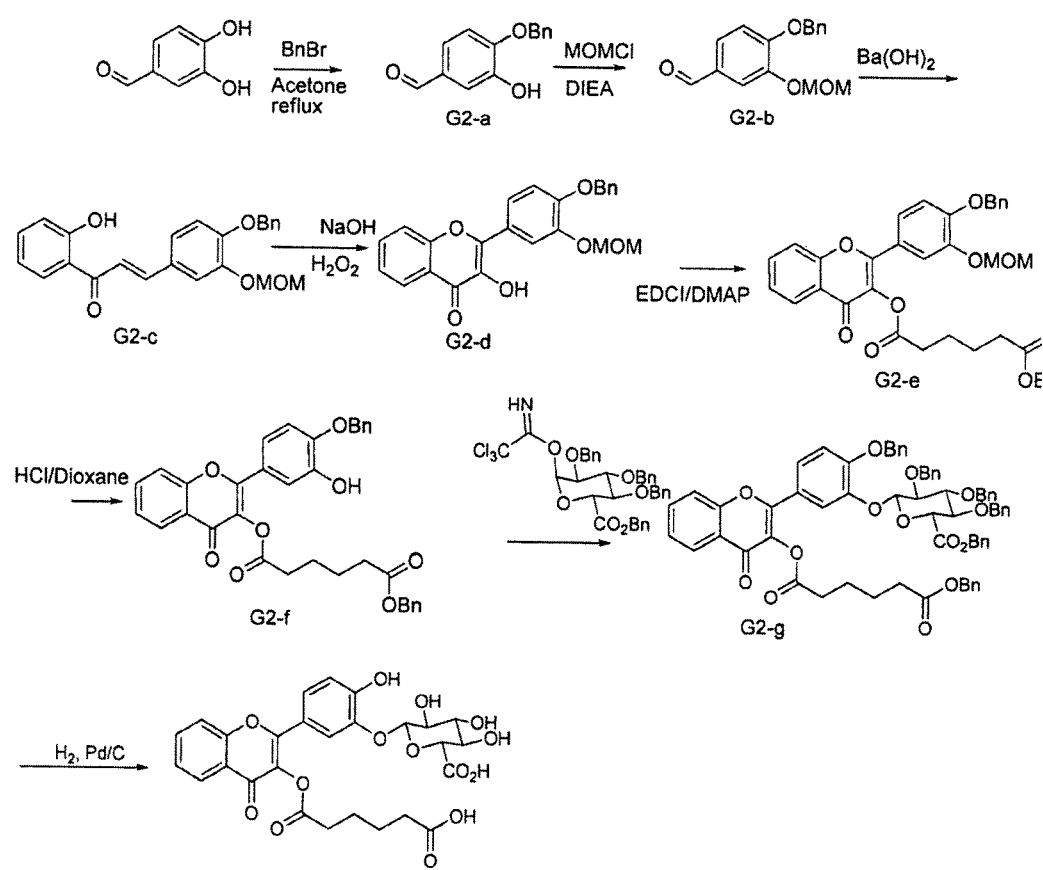
Figure 2: Synthesis of glucuronide 2 (17)

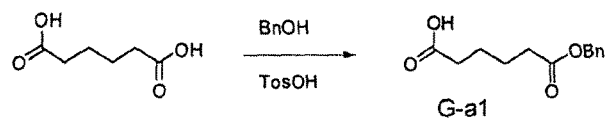
Figure 3: Synthesis of the side chain
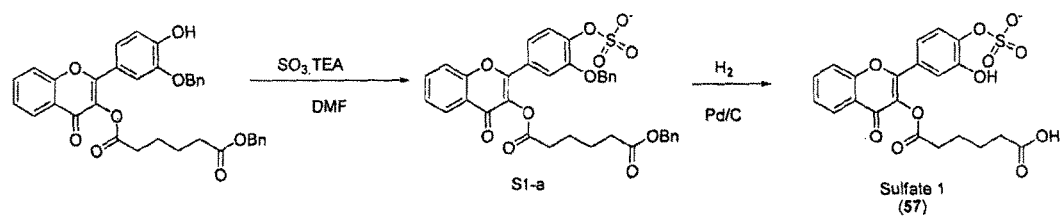
Figure 4: Synthesis of sulfate 1 (57)
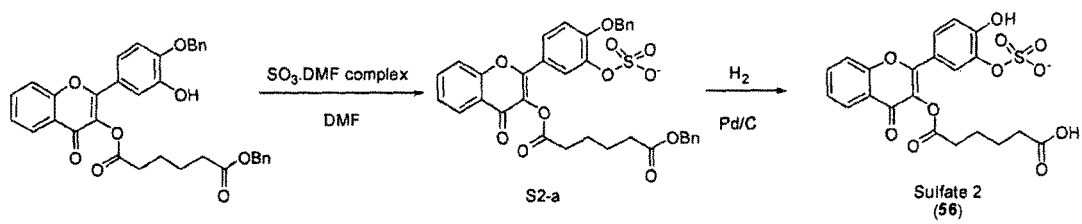
Figure 5: Synthesis of sulfate 2 (56)

FLAVONOID COMPOUNDS AND USES THEREOF

TECHNICAL FIELD

The present disclosure relates to novel compounds, compositions containing these compounds, methods for their synthesis, and uses of these compounds. In particular, the present disclosure relates to novel flavonoid compounds, methods of synthesizing the flavonoid compounds, compositions containing the flavonoid compounds and methods of their use.

BACKGROUND

Ischemic heart disease (IHD) and ischemic strokes are a major problem with our aging society and are the most common causes of death in most Western countries, and a major cause of hospital admissions.

During a heart attack or failure, reduced blood supply to the heart muscle can lead to severe tissue damage and death. Prompt reperfusion of ischemic tissue is critical for restoring normal function. However, this return of blood flow can paradoxically produce a progressive destruction of reversibly damaged cells, thereby leading to tissue dysfunction and infarction. This "reperfusion injury" has multifactorial causes of disease but appears to be strongly associated with an inflammatory response; with the return of blood flow, several inflammatory processes may occur to potentiate ischemic injury, including leukocyte adhesion and infiltration and the release of reactive oxidative species (ROS) such as oxygen free radical species and peroxides, for example $H_2O_2$.

Diabetic cardiomyopathy (DCM) is an increasingly recognized cause of congestive heart failure among diabetic patients. Oxidative stress is one of the common pathological changes associated with the development of DCM leading to the maladaptation of the left ventricular remodelling processes, manifested as abnormal cardiac function and can lead to ischaemia of the heart tissue.

Ischaemia can be caused by a variety of conditions. For example, acute incidents such as stroke, myocardial infarction or mechanical trauma, and chronic conditions such as atherosclerosis, peripheral vascular disease and diabetes can cause ischaemia. Hypertension is another type of disorder that can lead to ischaemia.

Following an acute incident such as a heart attack caused by a blocked coronary artery, various drugs are delivered intravenously to the heart attack victim to assist in removing any blood vessel obstruction thus re-establishing blood flow leading to reperfusion of tissues. However, this type of treatment is not directed to preventing or ameliorating the tissue damage associated with reperfusion. Creating an environment for reperfusion to occur and re-establish the supply of oxygen to tissue can lead to increased tissue damage by increasing free radical production.

Conventional treatments for subjects exhibiting ischaemia or at risk of ischaemia are inadequate and effective treatment regimes are urgently required.

One approach for preventing and/or mitigating the damage caused by ischaemia/reperfusion injuries has been to administer compounds which have antioxidant properties. For example, the synthetic flavonoid, 3',4'-dihydroxy flavonol (DiOHF) has been demonstrated to reduce infarct and injury associated with myocardial ischaemia and reperfusion during in vitro studies (Shen Wang, Gregory Dusting, Clive May and Owen Woodman, British Journal of Pharmacology (2004) 142, 443-452), but has poor pharmacokinetic properties.

Previous attempts to improve the pharmacokinetics of flavonoid compounds have focussed on the attachment of solubilising groups on the flavonoid ring. See for example, WO 2006/094357 Entitled "Flavonoid compounds and uses thereof" which describes improving the water solubility of a number of flavonoid compounds.

The poor pharmacokinetics of many flavonoids has severely limited their therapeutic usefulness. These characteristics limit their applicability to therapies where acute parenteral administration is desirable, for example in vasodilation therapies. Moreover, the use of other routes of administration, for example, oral, has been limited by the properties of the available flavonoid compounds.

Flavonoid compounds have the following general structure:

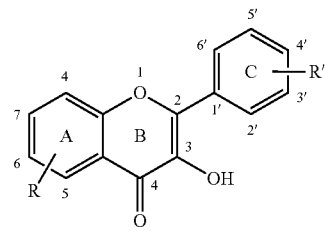

There is therefore a need for novel flavonoid compounds that have good biological activity and improved pharmacokinetic properties.

SUMMARY

It has now surprising been discovered, that the pharmacokinetic properties of certain flavonoid derivatives may be improved by the attachment of at least one non-solubilising protecting group. This is in contrast with traditional approaches which have focussed on the attachment of groups which increase the water solubility of the flavonoid compound.

According to a first aspect, there is disclosed a compound of the general Formula I:

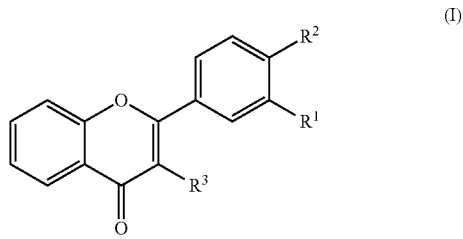

wherein
$R^1$, $R^2$, $R^3$ are independently selected from H or $OR^6$;
$R^6$ is $R^7$ or $R^8$;
$R^7$ is selected from the group comprising H, an ester, a carboxylic acid, sulfonic acid, sulphate, phosphonic acid, phosphate ester, sulfamate, sulfonic ester, phosphamate, phosphonate ester, sulfonate, zwitterionic species, amino acid, amino phosphonate, acyclic amine, cyclic amine, quaternary ammonium cation, polyethylene glycol, saccharide, oligosaccharide, polysaccharide, and dendrimer;

$R^8$ is selected from the group comprising H, saccharide, oligosaccharide, polysaccharide, sulfonate, a substituted or unsubstituted alkyl, alkenyl, alkynyl, aryl, cycloalkyl and acyl, optionally interrupted by one or more heteroatom(s); or a pharmaceutically acceptable salt, hydrate, solvate, prodrug and isomer thereof.

with the proviso that the compound includes at least one $R^7$ and at one least $R^8$ and that at least one of $R^7$ or $R^8$ is other than H;

with the further proviso that
when $R^2$ and $R^3$ are both OH, $R^1$ is not —OCH$_3$;
when $R^1$ and $R^2$ are both OH, $R^3$ is not —OC(O)-(CH$_2$)$_4$CO$_2$H;
when $R^1$ is H and $R^2$ is OH, $R^3$ is not —OC(O)-(CH$_2$)$_4$CO$_2$H.

In one embodiment, $R^7$ can be selected from an ester, carboxylic acid, sulfonic acid, phosphonic acid, phosphate ester, polyethylene glycol, saccharide and dendrimer.

In certain embodiments, $R^7$ can be a saccharide. In certain embodiments, the saccharide can be selected from a monosaccharide, oligosaccharide and polysaccharide.

In one embodiment, the saccharide can be a monosaccharide. The monosaccharide can be selected from the group comprising glucose, glucuronic acid, galactose, xylose, apiose, and allose. In one embodiment, the monosaccharide can be a glucuronic acid derivative. The glucuronic acid derivative can be

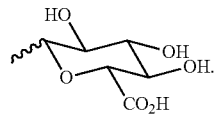

In another embodiment, $R^7$ can be a sulfonate. In a particular embodiment, $R^7$ can be a

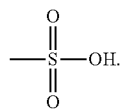

In another embodiment, $R^7$ can be selected from an ester, carboxylic acid or phosphate ester.

In another embodiment, $R^7$ can be a group according to:

wherein
W is O, NH, S, O—, NH$^-$ or S$^-$; and
X is H, a mono- or divalent cationic salt, or an ammonium cationic salt.

In one example, W is O and/or X is H.
In another embodiment, $R^7$ can be an ester according to:

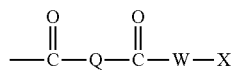

wherein
Q can be a substituted or unsubstituted lower alkylene, lower alkenylene, lower alkynylene, optionally interrupted by one or more heteroatom(s);
W is O, NH, S, O$^-$, NH$^-$, or S$^-$; and
X is H, a mono- or divalent cationic salt, or an ammonium cationic salt.

In another embodiment, $R^7$ can be an ester according to:

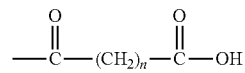

wherein
n can be an integer less than 10. One example includes where n can be an integer less than 7. In a certain embodiment, n is 4.

In one alternative embodiment, $R^7$ can be an ester according to:

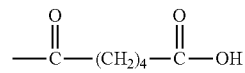

In one embodiment, $R^8$ can be selected from the group comprising a lower substituted or unsubstituted alkyl, alkenyl or alkynyl, cycloalkyl, aryl, acyl, optionally interrupted by one or more heteroatom(s).

In another embodiment, $R^8$ can be a substituted or unsubstituted lower alkyl, alkenyl or alkynyl, cycloalkyl group, optionally interrupted by one or more heteroatom(s).

In one embodiment, $R^8$ can be a substituted or unsubstituted lower alkyl. Particular embodiments, the lower alkyl can be a methyl, ethyl, n-propyl, iso-propyl, 2, n-butyl, sec-butyl, iso-butyl, tertbutyl, octa-decyl or 2-methylpentyl. In one particular embodiment, $R^8$ can be methyl.

In certain embodiments, $R^8$ can be selected from the group comprising a saccharide, oligosaccharide and polysaccharide.

In a certain embodiment, $R^8$ can be a saccharide. In one embodiment, the saccharide can be a monosaccharide. The monosaccharide can be selected from the group comprising glucose, glucuronic acid, galactose, xylose, apiose, and allose. In one embodiment, the monosaccharide can be a glucuronic acid derivative. The glucuronic acid derivative can be

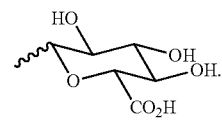

In another embodiment, $R^8$ can be a sulphate. In a particular embodiment, $R^8$ can be

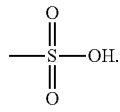

In another embodiment, $R^8$ can be an acyl group according to:

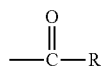

wherein R can be a substituted or unsubstituted lower alkyl, alkenyl or alkynyl, cycloalkyl group, optionally interrupted by one or more heteroatom(s).

In one embodiment, R can be a lower alkyl. In a particular embodiment, R can be a methyl group. In another embodiment, R can be a —C(CH$_3$)$_3$ group.

TABLE 1

Non-limiting examples of compounds in accordance with general formula (I).

| | R$^1$ | R$^2$ | R$^3$ |
|---|---|---|---|
| (1) | —O—C(=O)—CH$_3$ | —O—C(=O)—CH$_3$ | —O—C(=O)(CH$_2$)$_4$C(=O)—OH |
| (2) | —OCH$_3$ | —O—C(=O)—CH$_3$ | —O—C(=O)(CH$_2$)$_4$C(=O)—OH |
| (3) | —O—C(=O)—CH$_3$ | —OCH$_3$ | —O—C(=O)(CH$_2$)$_4$C(=O)—OH |
| (4) | —O—C(=O)—C(CH$_3$)$_3$ | —O—C(=O)—C(CH$_3$)$_3$ | —O—C(=O)(CH$_2$)$_4$C(=O)—OH |
| (5) | —O—C(=O)—CH$_3$ | —O—C(=O)—C(CH$_3$)$_3$ | —O—C(=O)(CH$_2$)$_4$C(=O)—OH |
| (6) | —O—C(=O)—C(CH$_3$)$_3$ | —O—C(=O)—CH$_3$ | —O—C(=O)(CH$_2$)$_4$C(=O)—OH |
| (7) | —O—C(=O)(CH$_2$)$_4$C(=O)—OH | —O—C(=O)(CH$_2$)$_4$C(=O)—OH | —O—C(=O)—CH$_3$ |
| (8) | —O—C(=O)(CH$_2$)$_4$C(=O)—OH | —O—C(=O)—CH$_3$ | —O—C(=O)—CH$_3$ |
| (9) | —O—C(=O)—CH$_3$ | —O—C(=O)(CH$_2$)$_4$C(=O)—OH | —O—C(=O)—CH$_3$ |
| (10) | —O—C(=O)(CH$_2$)$_4$C(=O)—OH | —O—C(=O)(CH$_2$)$_4$C(=O)—OH | —O—C(=O)—C(CH$_3$)$_3$ |
| (11) | —O—C(=O)(CH$_2$)$_4$C(=O)—OH | —O—C(=O)—C(CH$_3$)$_3$ | —O—C(=O)—C(CH$_3$)$_3$ |
| (12) | —O—C(=O)—C(CH$_3$)$_3$ | —O—C(=O)(CH$_2$)$_4$C(=O)—OH | —O—C(=O)—C(CH$_3$)$_3$ |
| (13) | —O—C(=O)(CH$_2$)$_4$C(=O)—OH | —O—C(=O)(CH$_2$)$_4$C(=O)—OH | —OCH$_3$ |
| (14) | —OCH$_3$ | —O—C(=O)(CH$_2$)$_4$C(=O)—OH | —OCH$_3$ |

TABLE 1-continued

Non-limiting examples of compounds in accordance with general formula (I).

| | R¹ | R² | R³ |
|---|---|---|---|
| (15) | —O—C(=O)(CH₂)₄C(=O)—OH | —OCH₃ | —OCH₃ |
| (16) | —O—C(=O)—CH₃ | —O—C(=O)—CH₃ | —O—C(=O)—CH₃ |
| (17) | methyl glucuronate group | —OH | —O—C(=O)(CH₂)₄C(=O)—OH |
| (18) | —OH | methyl glucuronate group | —O—C(=O)(CH₂)₄C(=O)—OH |
| (19) | methyl glucuronate group | methyl glucuronate group | —O—C(=O)(CH₂)₄C(=O)—OH |
| (20) | methyl glucuronate group | —O—C(=O)—CH₃ | —O—C(=O)(CH₂)₄C(=O)—OH |
| (21) | methyl glucuronate group | —O—C(=O)—CH₃ | methyl glucuronate group |
| (22) | —O—C(=O)—CH₃ | methyl glucuronate group | —O—C(=O)(CH₂)₄C(=O)—OH |
| (23) | —O—C(=O)—CH₃ | methyl glucuronate group | methyl glucuronate group |
| (24) | methyl glucuronate group | methyl glucuronate group | —O—C(=O)—CH₃ |
| (25) | methyl glucuronate group | —O—C(=O)—C(CH₃)₃ | —O—C(=O)(CH₂)₄C(=O)—OH |
| (26) | methyl glucuronate group | —O—C(=O)—C(CH₃)₃ | methyl glucuronate group |

TABLE 1-continued

Non-limiting examples of compounds in accordance with general formula (I).

| | R¹ | R² | R³ |
|---|---|---|---|
| (27) | glucuronic acid (HO, OH, OH, CO₂H) with O-linkage | —O—C(=O)—C(CH₃)₃ | —OH |
| (28) | —O—C(=O)—C(CH₃)₃ | glucuronic acid (HO, OH, OH, CO₂H) | —O—C(=O)—(CH₂)₄—C(=O)—OH |
| (29) | —O—C(=O)—C(CH₃)₃ | glucuronic acid (HO, OH, OH, CO₂H) | glucuronic acid (HO, OH, OH, CO₂H) |
| (30) | —O—C(=O)—C(CH₃)₃ | glucuronic acid (HO, OH, OH, CO₂H) | —OH |
| (31) | glucuronic acid (HO, OH, OH, CO₂H) | glucuronic acid (HO, OH, OH, CO₂H) | —O—C(=O)—C(CH₃)₃ |
| (32) | glucuronic acid (HO, OH, OH, CO₂H) | —OCH₃ | —O—C(=O)—(CH₂)₄—C(=O)—OH |
| (33) | glucuronic acid (HO, OH, OH, CO₂H) | —OCH₃ | glucuronic acid (HO, OH, OH, CO₂H) |
| (34) | —OCH₃ | glucuronic acid (HO, OH, OH, CO₂H) | —O—C(=O)—(CH₂)₄—C(=O)—OH |
| (35) | —OCH₃ | glucuronic acid (HO, OH, OH, CO₂H) | glucuronic acid (HO, OH, OH, CO₂H) |
| (36) | glucuronic acid (HO, OH, OH, CO₂H) | glucuronic acid (HO, OH, OH, CO₂H) | —OCH₃ |
| (37) | glucuronic acid (HO, OH, OH, CO₂H) | —OCH₃ | —OH |

TABLE 1-continued

Non-limiting examples of compounds in accordance with general formula (I).

| | R$^1$ | R$^2$ | R$^3$ |
|---|---|---|---|
| (38) | —OCH$_3$ | [sugar with OMe, OH, OH, OH, CO$_2$H] | —OH |
| (39) | [sugar with OMe, OH, OH, OH, CO$_2$H] | [sugar with OMe, OH, OH, OH, CO$_2$H] | —OH |
| (40) | —OH | —OH | [sugar with OMe, OH, OH, OH, CO$_2$H] |
| (41) | —OH | [sugar with OMe, OH, OH, OH, CO$_2$H] | —OH |
| (42) | [sugar with OMe, OH, OH, OH, CO$_2$H] | —OH | —OH |
| (43) | [sugar with OMe, OH, OH, OH, CO$_2$H] | —OH | [sugar with OMe, OH, OH, OH, CO$_2$H] |
| (44) | —OH | [sugar with OMe, OH, OH, OH, CO$_2$H] | [sugar with OMe, OH, OH, OH, CO$_2$H] |
| (45) | [sugar with OMe, OH, OH, OH, CO$_2$H] | [sugar with OMe, OH, OH, OH, CO$_2$H] | [sugar with OMe, OH, OH, OH, CO$_2$H] |
| (46) | —OH | —OH | —O—S(=O)$_2$—OH |
| (47) | —OH | —O—S(=O)$_2$—OH | —OH |
| (48) | —O—S(=O)$_2$—OH | —OH | —OH |
| (49) | —O—S(=O)$_2$—OH | —O—S(=O)$_2$—OH | —OH |

TABLE 1-continued

Non-limiting examples of compounds in accordance with general formula (I).

| | R¹ | R² | R³ |
|---|---|---|---|
| (50) | —O—S(=O)₂—OH | —OH | —O—S(=O)₂—OH |
| (51) | —OH | —O—S(=O)₂—OH | —O—S(=O)₂—OH |
| (52) | —O—S(=O)₂—OH | —O—C(=O)(CH₂)₄C(=O)—OH | —OH |
| (53) | —O—C(=O)(CH₂)₄C(=O)—OH | —O—S(=O)₂—OH | —OH |
| (54) | —O—C(=O)(CH₂)₄C(=O)—OH | —OH | —O—S(=O)₂—OH |
| (55) | —OH | —O—C(=O)(CH₂)₄C(=O)—OH | —O—S(=O)₂—OH |
| (56) | —O—S(=O)₂—OH | —OH | —O—C(=O)(CH₂)₄C(=O)—OH |
| (57) | —OH | —O—S(=O)₂—OH | —O—C(=O)(CH₂)₄C(=O)—OH |
| (58) | —O—S(=O)₂—OH | —O—S(=O)₂—OH | —O—C(=O)(CH₂)₄C(=O)—OH |
| (59) | —O—S(=O)₂—OH | —O—C(=O)(CH₂)₄C(=O)—OH | —O—S(=O)₂—OH |
| (60) | —O—C(=O)(CH₂)₄C(=O)—OH | —O—S(=O)₂—OH | —O—S(=O)₂—OH |
| (61) | —O—C(=O)(CH₂)₄C(=O)—OH | —O—C(=O)(CH₂)₄C(=O)—OH | —O—S(=O)₂—OH |

TABLE 1-continued
Non-limiting examples of compounds in accordance with general formula (I).
| | R¹ | R² | R³ |
|---|---|---|---|
| (62) | 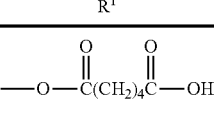 | 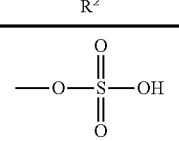 | 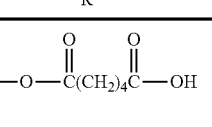 |
| (63) | 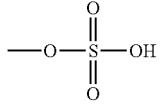 | 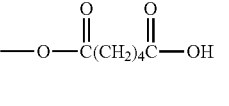 | 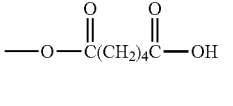 |
| (64) | 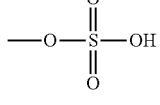 | —OH |  |
| (65) | —OH | 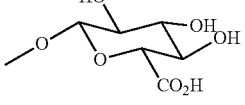 |  |
| (66) | 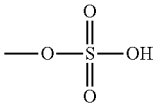 | 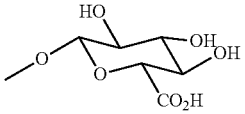 | —OH |
| (67) | 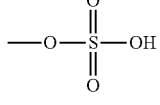 | 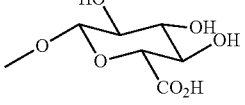 | —OH |
| (68) | —OH |  | 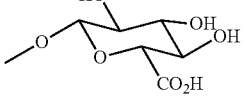 |
| (69) | 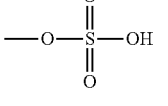 | —OH |  |
| (70) |  | 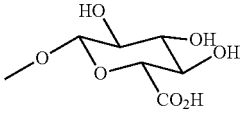 | 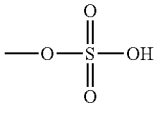 |
| (71) | 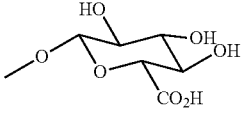 |  | 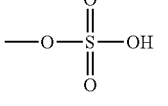 |
| (72) | 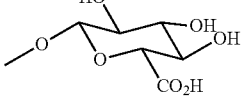 | 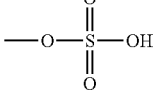 | 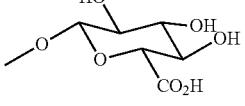 |
| (73) | 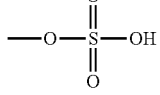 | 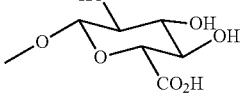 | 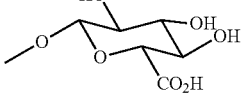 |

TABLE 1-continued

Non-limiting examples of compounds in accordance with general formula (I).

| | R¹ | R² | R³ |
|---|---|---|---|
| (74) | —O—S(=O)(=O)—OH | [sugar with HO, OH, OH, CO₂H] | —O—S(=O)(=O)—OH |
| (75) | —O—S(=O)(=O)—OH | —O—S(=O)(=O)—OH | [sugar with HO, OH, OH, CO₂H] |
| (76) | —O—C(=O)(CH₂)₄C(=O)—OH | —O—C(=O)(CH₂)₄C(=O)—OH | —O—C(=O)(CH₂)₄C(=O)—OH |
| (77) | —O—C(=O)—C(CH₃)₃ | —O—C(=O)—C(CH₃)₃ | —O—C(=O)—C(CH₃)₃ |

One aspect relates to a method of preventing and/or treating a disease(s) in a subject associated with the presence of reactive oxidative species (ROS), the method comprising:

administering an effective amount of at least one compound disclosed above.

In one embodiment, the subject in need of such treatment is at risk of developing ischaemia. In a particular embodiment, the subject is suffering ischaemia and/or reperfusion injury as a result of an acute or chronic condition.

While not wishing to be bound by theory, it is thought that the present compounds can also assist in maintaining and/or improving circulatory flow. For example, the present compounds may be administered to a patient with diabetes to assist in management of the disease.

The chronic condition may be selected from cancer, cerebrovascular disease, pulmonary vascular disease, atherosclerosis, artery disease, congestive heart disease, coronary disease, peripheral vascular disease, diabetes, hypertension, migraine, burns, chronic obstructive pulmonary disease and retinal vascular disease.

The acute condition may be selected from stroke, myocardial infarction, mechanical trauma resulting from crush injury or surgery. In a particular embodiment, the vascular surgery is heart bypass and/or transplant surgery.

The disclosed compounds may be administered to the subject before and/or during the surgery.

Another aspect relates to a method of preventing, delaying the onset of and/or slowing the progression of atherosclerosis and/or coronary heart disease in a subject comprising administering an effective amount of at least one compound disclosed above.

Another aspect relates to a therapeutic and/or prophylactic method of preventing and/or treating a disease(s) in a subject associated with the presence of reactive oxidative species (ROS), the method comprising:

administering an effective amount of at least one of the disclosed compounds.

Another aspect relates to a method of preventing and/or at least ameliorating the damage to a subject caused by ischaemia and/or reperfusion injury, the method comprising administering an effective amount of at least one compound disclosed above.

Another aspect relates to a method of preventing and/or at least ameliorating damage to a subject caused by the administration of a therapeutic agent, the method comprising co-administering to a subject:

i) a therapeutic agent; and ii) administering an effective amount of at least one compound disclosed above.

Therapeutic agent may be an oxidative therapeutic agent. A particular example of a therapeutic agent is an anticancer agent. In particular, the anticancer agent may be anthracycline and its derivatives.

In particular embodiments, the disclosed compound(s) is administered orally, topically, subcutaneous, parenterally, intramuscular, intra-arterial and/or intravenously. In a particular embodiment, the compound is administered orally.

In another aspect, there is disclosed the use of a compound as specified above for the preparation of a medicament.

In yet another aspect there is disclosed a method for synthesizing compounds as specified above.

The formulae given herein are intended to extend to all possible geometric and optical isomers as well as racemic mixtures thereof.

In another aspect there is disclosed a pharmaceutical and/or a veterinary composition comprising a pharmaceutically and/or veterinarily acceptable carrier or diluent together with at least one compound compounds as specified above or a pharmaceutically acceptable salt or solvates thereof.

In another aspect there is disclosed a method of preventing and/or at least ameliorating damage to a subject caused by the administration of a therapeutic agent, the method comprising co-administering to a subject:

i) a therapeutic agent; and ii) an effective amount of at least one compound in accordance with Formula (I) as disclosed above, or a pharmaceutically acceptable salt or solvates thereof.

In yet another aspect, there is disclosed a method of preventing and/or treating a disease(s) associated with the presence of reactive oxidative species (ROS), the method comprising administering an effective amount of at least one compound in accordance with Formula (I) as disclosed above, or a pharmaceutically acceptable salt or solvates thereof.

In another aspect there is disclosed a method of preventing and/or treating a disease(s) associated with the presence of reactive oxidative species (ROS), the method comprising administering an effective amount of at least one compound in accordance with Formula (I) as specified above, or a pharmaceutically acceptable salt or solvates thereof.

Typically the subject in need of such treatment will be a person at risk of developing ischaemia. Alternatively, the subject may be a person who is currently suffering ischaemia and/or reperfusion as a result of an acute or chronic condition.

In another aspect there is disclosed a method of preventing and/or at least ameliorating the damage to a subject caused by ischaemia and/or reperfusion, the method comprising administering an effective amount of at least one compound in accordance with Formula (I) as specified above, or a pharmaceutically acceptable salt or solvates thereof, or a pharmaceutically acceptable salt or solvates thereof.

It is desirable that the presence of at least one solubilising group renders the compound at least partially soluble, and more preferably, totally soluble in aqueous solution, preferably water.

DESCRIPTION OF EMBODIMENTS

According to a first aspect, there are disclosed flavonoid derivatives and compositions containing flavonoid derivatives, and methods of using same.

The presence of reactive oxidative species (ROS) in living tissue has been shown to be associated with many disorders in animals. Reactive oxidative species can contain both nitrogen and oxygen, or only oxygen atoms. Some examples of ROS molecules include singlet $O_2$, $H_2O_2$, free radicals such as OH., $O_2^-$., NO., and ROO.. Many of these species are formed during normal metabolic activity, but their concentration levels can be elevated under conditions of oxidative stress associated with chronic inflammation, infections and other diseases.

Many ROS molecules are the result of naturally occurring processes such as oxygen metabolism and inflammatory processes. For example, when cells use oxygen to generate energy, free radicals are created as a consequence of ATP production by the mitochondria. Exercise can increase the levels of free radicals as can environmental stimuli such as ionizing radiation (from industry, sun exposure, cosmic rays, and medical X-rays), environmental toxins, altered atmospheric conditions (e.g. hypoxia and hyperoxia), ozone and nitrogen oxide (primarily from automobile exhaust, therapeutics). Lifestyle stressors such as cigarette smoking and excessive alcohol consumption are also known to affect levels of free radicals. Radical species may combine to form other more damaging or toxic species such as peroxynitrite ONOO$^-$, a product of superoxide and nitric oxide radical reaction.

Another source of ROS species is some therapeutic agents, such as anti-cancer drugs. Anthracycline derivatives are highly useful anti-cancer agents in the treatment of neoplastic diseases such as acute leukemia, malignant lymphoma, etc. However, an undesirable feature of their administration can be oxidative damage to tissue, which can lead to cardiomyopathy and possible heart failure. The presence of the therapeutic agent can therefore cause the development of congestive heart failure (CHF). This feature of some therapeutic agents can limit their effectiveness and it would be useful to develop an appropriate co-administration regime.

In another aspect, there is disclosed a method of treating a subject having a disease or disorder involving oxidative damage, comprising administering a therapeutically effective amount of a composition as disclosed.

Preferably, the disease or disorder involving oxidative damage is selected from the group consisting of cancer, heart disease, neurological disorders, auto-immune disorders, ischaemia-reperfusion injury, diabetic complications, septic shock, hepatitis, atherosclerosis, Alzheimer's disease and complications arising from HIV or Hepatitis, including Hepatitis B.

In one embodiment, the subject is an animal. The animal may be selected from the group consisting of humans, non-human primates, cattle, horses, pigs, sheep, goats, dogs, cats, birds, chickens or other poultry, ducks, geese, pheasants, turkeys, quails, guinea pigs, rabbits, hamsters, rats and mice.

In some aspects, the one or more disclosed flavonoid derivatives are administered simultaneously, separately or sequentially with the one or more therapeutic agent(s).

When used in such a combination the one or more therapeutic agent(s) and the one or more disclosed flavonoid derivative(s) can be administered as separate agents at the same or different times or they can be formulated as a single composition comprising both compounds.

Free radicals react with key organic substrates in cells such as lipids, proteins, and DNA. Oxidation of these biomolecules can damage them, disturbing normal functions and may contribute to a variety of disease states. It has been noted that certain organ systems are predisposed to greater levels of oxidative stress or nitrosative stress. Those organ systems most susceptible to damage are the pulmonary system (exposed to high levels of oxygen), the brain (exhibits intense metabolic activity yet has lower levels of endogenous antioxidants), the eye (constantly exposed to damaging UV light), circulatory system (victim to fluctuating oxygen and nitric oxide levels) and reproductive systems (at risk from the intense metabolic activity of sperm cells).

Examples of relevant acute disorders causing the production of ROS include ischaemia reperfusion, stroke, myocardial infarction or mechanical trauma, such as a crush injury or surgery. Some forms of surgery such as heart bypass or transplant surgery necessarily cause ischaemia and reperfusion of tissue. Typically one or more flavonoid derivatives according are administered to the subject before and/or during surgery.

Chronic disorders may be chosen from the group including cancer, cerebrovascular disease, atherosclerosis, artery disease including coronary disease, peripheral vascular disease (including damage caused by diseases such as diabetes), hypertension, pulmonary hypertension, chronic obstructive airways disease, emphysema, neurological disorders, auto-immune disorders, diabetic complications, septic and hypovolemic shock, burns, hepatitis, and complications arising from hepatitis and HIV. Another chronic disorder may be chosen from the complications resulting from administration of hyperbaric or high oxygen tension atmospheres, often applied to assist breathing particularly in a premature infant human, including retinal or other eye damage. Subjects at risk of relevant chronic disorders may be diagnosed by analysis of symptoms, diagnostic testing, enzymatic markers, or by genetic testing to identify a genetic predisposition. Predisposition to certain acute disorders such as heart attack or stroke may also be identified by genetic testing and may prompt the prophylactic application of one or more flavonoid derivatives to the subject at risk. Drug-induced disorders due to ROS e.g. drug induced congestive heart disease.

If the disease or disorder is stroke or risk or stroke, the composition described above is preferably administered before the stroke occurs as a prophylactic to reduce the risk of stroke occurrence, or within twelve hours (preferably within four hours) of stroke occurrence.

An example of an ROS involved pathological condition is ischaemia where a deficiency of blood flow to part of a body results in inadequate tissue perfusion with oxygen. Ischaemia causes tissue damage, the severity of the damage depending on the length of time the tissue is deprived of oxygen and whether adequate reperfusion of oxygen occurs after the ischaemic event.

At least one compound described herein may be administered via a number of different routes, for example, topically, orally, subcutaneous, intramuscular, intra-arterially and/or intravenously.

Definitions

As used herein, the term "alkyl" includes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups can be substituted or unsubstituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "lower" herein includes a linear or branched chain of 1 to 6 carbon atoms.

The term "alkylene" refers to a divalent alkyl as defined above, such as methylene (—$CH_2$—), propylene (—$CH_2CH_2CH_2$—), chloroethylene (—$CHClCH_2$—), 2-thiobutene-$CH_2CH(SH)CH_2CH_2$, 1-bromo-3-hydroxyl-4-methylpentene (—$CHBrCH_2CH(OH)CH(CH_3)CH_2$—), methylethylene, trimethylene, 1-propylene, 2-propylene, tetramethylene, 1-methyltrimethylene, 2-methyltrimethylene, 3-methyltrimethylene, 1-ethylethylene, 2-ethylethylene, pentamethylene, 1-methyltetramethylene, 2-methyltetramethylene, 3-methyltetramethylene, 4-methyltetramethylene and hexamethylene and the like.

The term "alkenyl" includes branched or unbranched hydrocarbon chains containing one or more carbon-carbon double bonds.

The term "alkynyl" includes branched or unbranched hydrocarbon chains containing one or more carbon-carbon triple bonds.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or tri-substituted. The aryl groups herein are unsubstituted or, as specified, substituted in one or more substitutable positions with various groups.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_1$-$C_6$ alkenyl, $C_1$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

The term "acyl" includes an —C(O)R group, wherein R is alkyl or aryl as defined above, such as formyl, acetyl, propionyl, or butyryl.

The term "alkoxy" includes —OR—, wherein R is alkyl. The term "lower alkoxy radicals" there may be mentioned linear and branched alkoxy groups of 1 to 6 carbon atoms, such as methoxy, ethoxy, propoxy, isopropoxy, butoxy, isobutoxy, sec-butoxy, tert-butoxy, pentyloxy, isopentyloxy, hexyloxy and isohexyloxy groups.

The term "amido" includes an amide linkage: —C(O) NR— (wherein R is hydrogen or alkyl).

The term "amino" indicates an amine linkage: —NR—, wherein R is hydrogen or alkyl.

The term "carboxyl" indicates —C(O)O—, and the term "carbonyl" indicates —C(O)—.

The term "carbonate" indicates —OC(O)O—.
The term "sulfonate" indicates —$S(O)_2O^-$.
The term "carboxylic acid" indicates —C(O)OH.
The term 'sulfonic acid" indicates —$S(O)_2OH$.
The term "phosphonic acid" indicates —$P(O)(OH)_2$.
The term "phosphamate" indicates —Ar—$NHPO_4^-$.
The term "phosphate ester" indicates —O—$P(O)(OR)_2$.
The term "sulfamate" indicates —Ar—$NHSO_3^-$.
The term "sulfonic esters" indicates —$S(O)_2$—OR.
The term "sulfonate" indicates —$S(O)_2O^-$.
The term "phosphonate ester" indicates R—$P(O)(OR)_2$.
The term "carbamate" indicates —NHC(O)O—.

Examples of a monosaccharide include: hexose such as allose, altrose, glucose, mannose, gulose, idose, galactose, or talose; pentose such as ribose, arabinose, xylose, or lyxose; tetrose such as erythrose or threose; and triose such as glyceraldehyde. In addition, sugars used herein include derivatives thereof. Examples of sugar derivatives include: reduced derivatives such as sugar alcohol, deoxy sugar, and glycal; oxidized derivatives such as aldonic acid, uronic acid, and aldaric acid; dehydrated derivatives such as glycoseen and anhydro sugar; phosphate-esterified products; acetate-esterified products; amino sugars; thio sugars; glycoproteins; sugar esters; and sugar ethers. In particular embodiments, the monosaccharide may be selected from among glucose, glucuronic acid, galactose, xylose, apiose, allose, rhamnose, arabinofuranose, and mannose. In some embodiments, the monosaccharide may be selected from among glucose, glucuronic acid, galactose, xylose, apiose, and allose. Most preferably, the monosaccharide may be glucose. Further, the monosaccharide may be in the D- or L-form but it is preferably in the D-form.

The hydrocarbon chains can be optionally interrupted by one or more heteroatoms.

I Compound Synthesis

In some aspects, there are disclosed flavonoid compounds according to Formula I and methods of synthesizing such compounds.

II Compositions and Methods

The compounds can be formulated in a variety of carriers and delivery systems. The amount of the therapeutic compound to be administered and the compound's concentration is dependent on the vehicle or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

Furthermore, excipients can be included in the formulation. Examples include co-solvents, surfactants, oils, humectants, emollients, preservatives, stabilizers and antioxidants. Any pharmacologically acceptable buffer may be used, e.g., Tris or phosphate buffers. Effective amounts of diluents, additives and excipients are those amounts which are effective to obtain a pharmaceutically acceptable formulation in terms of solubility, biological activity, etc.

Thus, a composition of the present disclosure may include a therapeutic compound which can be formulated with conventional, pharmaceutically acceptable, vehicles for topical, oral or parenteral administration. Formulations can also include small amounts of adjuvants such as buffers and preservatives to maintain isotonicity, physiological and pH stability.

III Administration

The compounds of the present disclosure may be administered to both human and animal subjects.

The compounds of the present disclosure may be administered in compositions wherein the active compound is intimately admixed with one or more inert ingredients and optionally including one or more additional active ingredients. The compounds may be used in any composition known to those skilled in the art for administration to humans and animals.

The compositions of the present disclosure may be administered through a proper route according to the dosage form. For example, the injection can be administered intravenous, intra-arterial, subcutaneous, intramuscular and the like.

For oral administration, either solid or fluid unit dosage forms can be prepared. The water soluble forms can be dissolved in an aqueous vehicle together with sugar, aromatic flavouring agents and preservatives to form syrup. An elixir is prepared by using a hydro-alcoholic (e.g., ethanol) vehicle with suitable sweeteners such as sugar and saccharin, together with an aromatic flavouring agent. Suspensions can be prepared with an aqueous vehicle with the aid of a suspending agent such as acacia, tragacanth, methylcellulose and the like. The synthetic flavonoid compounds may also be formulated with stabilizing agents, for example metal chelator reducing agents such as ethylenediaminetetracetic acid (EDTA) or a reducing agent such as sodium metabisulfite.

Appropriate formulations for parenteral use are apparent to the practitioner of ordinary skill. Usually, the therapeutic compound is prepared in an aqueous solution in a concentration of from about 1 to about 100 mg/mL. More typically, the concentration is from about 10 to 60 mg/mL or about 20 mg/mL. Concentrations below 1 mg/mL may be necessary in some cases depending on the solubility and potency of the compound selected for use. The formulation, which is sterile, is suitable for various parenteral routes including intradermal, intra-articular, intramuscular, intravascular, intravenous, inhalation and subcutaneous.

Compositions of the present disclosure may be formulated into sunscreens, skin care compositions, emollient of moisturizers.

The synthetic flavonoid compound(s) may also be formulated as a nutrapharmaceutical or a nutraceutical. For example, the synthetic flavonoid compound(s) may be formulated into a food, such as a cereal, beverages such as fruit juice, alcoholic drinks, bread, etc, for oral consumption.

Aspects of the present disclosure may be illustrated by the following non-limiting examples.

Example 1: Synthesis of 3',4'-Diacetoxyflavone 3-hemiadipate (1)

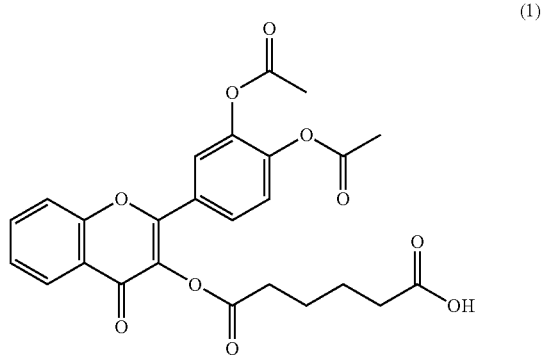 [SMILES: CC(=O)Oc1ccc(-c2oc3ccccc3c(=O)c2OC(=O)CCCCC(=O)O)cc1OC(C)=O]

A solution of 3',4'-dihydroxyflavone 3-hemiadipate (1 g, 2.51 mmol) and acetic anhydride (3 equivalents) in pyridine (5 mL) may be stirred at room temperature for 1 h. The reaction mixture may be diluted with aqueous HCl (1 M, 50 mL) and stirred vigorously for 15 min. The precipitate may then be collected by filtration and dried. The product can be purified by chromatography or recrystallization to afford 3',4'-diacetoxyflavone 3-hemiadipate.

Example 2: Synthesis of 3',4'-Dipivaloxyflavone 3-hemiadipate (4)

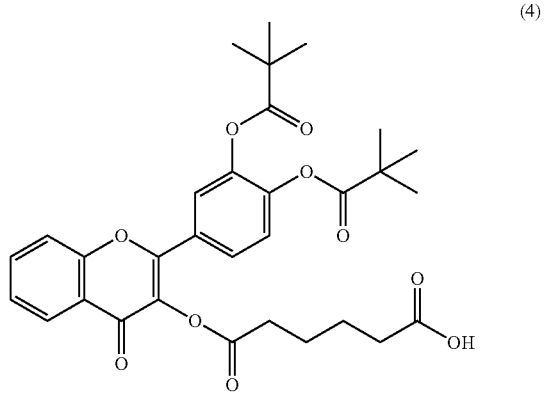 [SMILES: CC(C)(C)C(=O)Oc1ccc(-c2oc3ccccc3c(=O)c2OC(=O)CCCCC(=O)O)cc1OC(=O)C(C)(C)C]

A solution of 3',4'-dihydroxyflavone 3-hemiadipate (1 g, 2.51 mmol) and pivaloyl chloride (5 equivalents) in pyridine (5 mL) may be heated at 60° C. for 6 h. The reaction mixture can be diluted with aqueous HCl (1 M, 50 mL) and stirred vigorously for 15 min. The precipitate may be collected by filtration, dried and purified by chromatography or recrystallization to afford 3',4'-dipivaloxyflavone 3-hemiadipate.

Example 3: Biological Activity of Novel Flavonoid

To determine the antioxidant activity of the novel flavonoid compounds they may be tested in rat systems.

Animals and Procedures

Six week old male homozygous transgenic (mRen2) 27 rats (St. Vincent's Hospital Animal Resource Centre, Melbourne, Victoria, Australia) can be randomized to receive either 55 mg/kg of streptozotocin (STZ; Sigma, St Louis, Mo., USA) diluted in 0.1 mol/L citrate buffer pH 4.5 (diabetic) to induce experimental type 1 diabetes or citrate buffer alone (non-diabetic control) by tail vein injection following overnight fasting. Diabetic and control rats (n=10) may be further randomized to receive either an orally active synthetic antioxidant, 3',4'-Diacetoxyflavone 3-hemiadipate, at 1 mg/kg or vehicle (1% carboxy methyl cellulose solution; CMC) by daily gavage for six weeks post STZ. Animals can be housed in a stable environment maintained at 21±1° C. (12 hour light/dark cycle commencing at 6 am). Animals will have free access to standard rat chow (GR2 Clark-King and Co, Gladesville, NSW, Australia) and drinking water.

Each week, rats can be weighed and their blood glucose levels measured (Accucheck Advantage II Blood Glucose Monitor, Roche Diagnostics, USA). Only STZ-treated animals with blood glucose greater than 15 mmol/L may be considered diabetic. Prior to the induction of diabetes and every three weeks post randomization, systolic blood pressure (SBP) can be assessed in preheated conscious rats by tail cuff plethysmography using a non-invasive blood pressure (NIBP) controller and Powerlab system (AD Instruments Pty Ltd, NSW, Australia) 23, 24. Diabetic animals received 2-4 units of isophane insulin (Humulin NPH; Eli Lilly and Co., NSW, Australia) intraperitoneally 3 times per week to maintain blood glucose levels, promote weight gain and reduce mortality.

At the end of the experimental period, animals may be anaesthetized (Lethabarb 30 mg/kg body weight i.p.; Virbac, Peakhurst, NSW, Australia). The abdomen, neck, and chest may then be shaved, and echocardiography performed followed by in vivo left ventricular pressure-volume (PV) loop acquisition.

Example 4: Synthesis of Catechol Glucuronide Isomers (Counter-Ion not Shown)

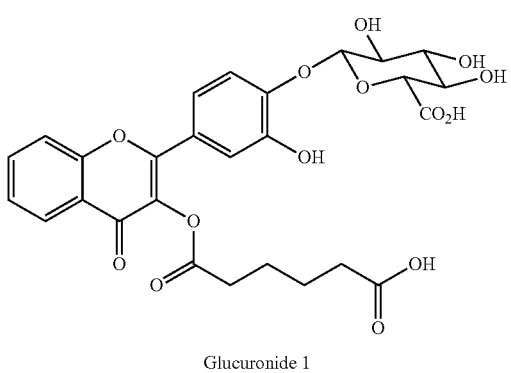

Glucuronide 1

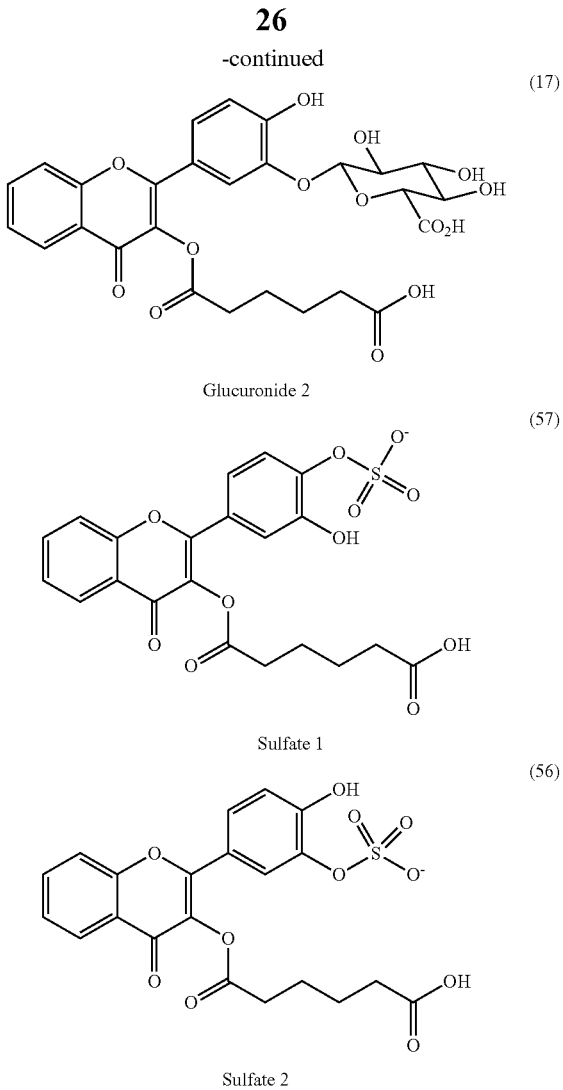

Glucuronide 2

Sulfate 1

Sulfate 2

Synthesis of G-a

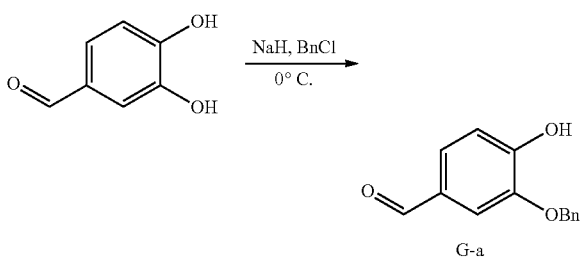

G-a

To a solution of 3,4-dihydroxybenzaldehyde (5.0 g, 36.2 mmol) in DMF (100 mL) at 0° C. under $N_2$ was added NaH (60% dispersion in mineral oil, 2.90 g, 72.4 mmol) and the mixture was stirred at 0° C. for 0.5 h. Benzyl chloride (4.12 g, 32.6 mmol) was then added dropwise and stirring was continued at 0° C. for 12 h. The mixture was diluted with water (200 mL), extracted with EtOAc and the organic extracts were dried over $Na_2SO_4$, filtered and concentrated in vacuo. The residue was purified by column chromatography (EtOAc/Pet. Ether, 0-25%, v/v) followed by rinsing with a 25% EtOAc/Pet. ether solution to give the product, which contained a small amount of the undesired 4-benzyloxy isomer (G2-a). Further purification by column chromatography (DCM/Pet. Ether, 0-100%, v/v) then enabled separation and gave the desired product G-a (4.5 g, 60%) and the minor isomer G2-a (0.3 g, 4%) as white solids. TLC: $R_f$=0.70 (silica gel, Pet.ether/EtOAc=4/1, v/v); LCMS: m/z 229.1 [M+H]$^+$, 251.0 [M+Na]+; $^1$HNMR: (400 MHz, CDCl$_3$) δ ppm 9.77 (s, 1H), 7.50 (d, J=1.6 Hz, 1H), 7.41 (m, 6H), 7.06 (d, J=8.0 Hz, 1H), 6.54 (s, 1H), 5.15 (s, 2H).

Synthesis of G-b

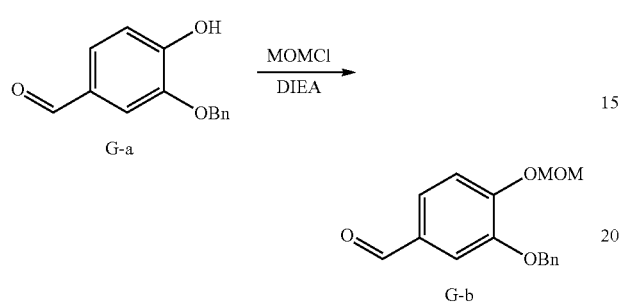

To a solution of intermediate G-a (4.40 g, 19.3 mmol) in DCM (100 mL) was added DIPEA (4.98 g, 38.4 mmol) followed by MOMCl (2.32 g, 28.9 mmol) and the mixture was stirred at RT for 5 h. The solvent was removed in vacuo and the residue was diluted with water and extracted with EtOAc (200 mL). The organic extracts were washed with a 1 M aqueous HCl solution (×2), brine, dried over Na$_2$SO$_4$, filtered and concentrated in vacuo to give the product (5.0 g, 95%) as yellow oil, which was used directly in next step without further purification. TLC: $R_f$=0.75 (silica gel, Pet.ether/EtOAc=4/1, v/v); $^1$HNMR: (400 MHz, CDCl$_3$) δ ppm 9.85 (s, 1H), 7.51-7.27 (m, 8H), 5.34 (s, 2H), 5.22 (s, 2H), 3.54 (s, 3H).

Synthesis of G-c

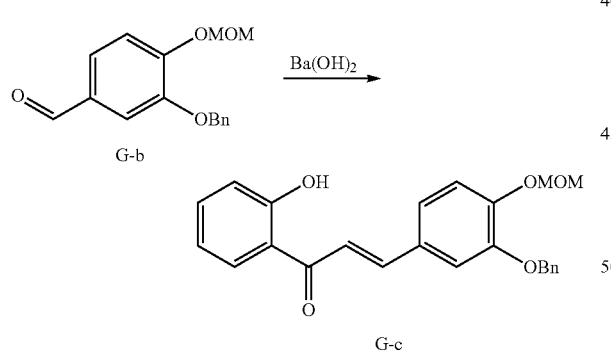

A mixture of intermediate G-b (5.0 g, 18.4 mmol), 1-(2-hydroxyphenyl) ethanone (2.50 g, 18.36 mmol) and Ba(OH)$_2$ (6.29 g, 36.7 mmol) in MeOH (120 mL) was heated at 40° C. overnight. The mixture was diluted with EtOAc and the solid was collected by filtration. The filter cake was taken up in a dilute aqueous HCl solution and extracted with EtOAc. The combined organic extracts were washed with brine, dried over Na$_2$SO$_4$, filtered and concentrated in vacuo to give the product (6.80 g, 95%) as yellow oil, which was used directly in the next step without further purification. TLC: $R_f$=0.70 (silica gel, Pet.ether/EtOAc=5/1, v/v).

Synthesis of G-d

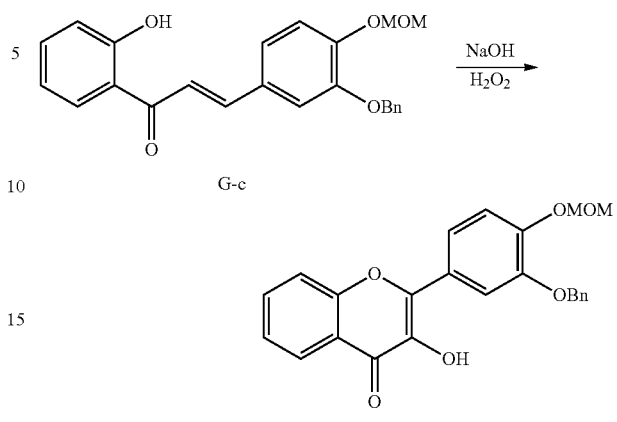

To a solution of intermediate G-c (6.80 g, 17.4 mmol) in MeOH (100 mL) at 0° C. was added a 5.6% aqueous NaOH solution (56 mL) followed by H$_2$O$_2$ (30%, 6.46 mL) dropwise and the mixture was stirred at 0° C. for 2 h, then allowed to warm slowly to RT and stirred overnight. The mixture was poured into a dilute aqueous HCl solution and extracted with EtOAc. The organic extract was dried over Na$_2$SO$_4$, filtered and concentrated in vacuo. The residue was washed with EtOH and dried in vacuo to give the product (4.93 g, 70%) as a yellow solid. TLC: $R_f$=0.45 (silica gel, Pet.ether/EtOAc=4/1, v/v); LCMS: m/z 405.1 [M+H]$^+$, 427.1 [M+Na]$^+$; $^1$HNMR: (400 MHz, DMSO-d) δ ppm 9.53 (br s, 1H), 8.08 (dd, J=8.0, 1.2 Hz, 1H), 7.92 (d, J=2.0 Hz, 1H), 7.83-7.71 (m, 3H), 7.51-7.38 (m, 5H), 7.34 (m, 1H), 7.24 (d, J=8.8 Hz, 1H), 5.26 (s, 2H), 5.19 (s, 2H), 3.40 (s, 3H).

Synthesis of G-e

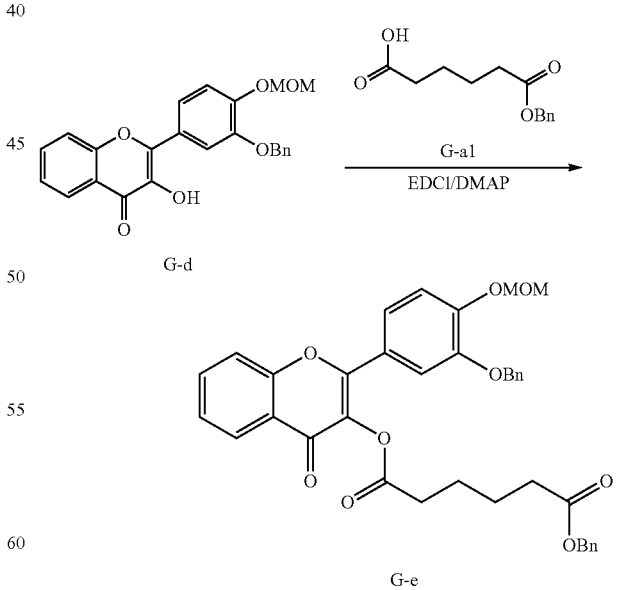

To a solution of intermediate G-d (1.50 g, 3.71 mmol) and intermediate G-a1 (1.67 g, 7.05 mmol) in DCM (60 mL) was added EDCI (1.06 g, 5.56 mmol) followed by DMAP (0.45 g, 3.71 mmol) and the mixture was stirred at RT for 48 h.

The solvent was removed in vacuo and the residue was diluted with water and extracted with EtOAc (100 mL). The organic extract was washed with a saturated aqueous $K_2CO_3$ solution, a dilute aqueous HCl solution, brine and dried over $Na_2SO_4$, filtered and concentrated in vacuo. The residue was purified by column chromatography (DCM/Pet. Ether, 0-100%, v/v) to give the product (1.70 g, 73%) as a yellow oil. TLC: $R_f$=0.30 (silica gel, Pet.ether/EtOAc=4/1, v/v); LCMS: m/z 623.2 [M+H]+, 645.2 [M+Na]$^+$; HNMR: (400 MHz, DMSO-$d_6$) δ ppm 8.07 (dd, J=8.0, 1.4 Hz, 1H), 7.88 (m, 1H), 7.77 (d, J=8.4 Hz, 1H), 7.60 (d, J=2.0 Hz, 1H), 7.51 (m, 4H), 7.41 (m, 2H), 7.34-7.26 (m, 7H), 5.29 (s, 2H), 5.20 (s, 2H), 5.07 (s, 2H), 3.39 (s, 3H), 2.58 (m, 2H), 2.37 (m, 2H), 1.61 (m, 4H).

Synthesis of G-f

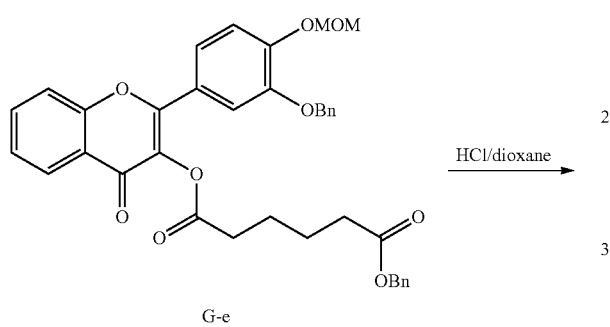

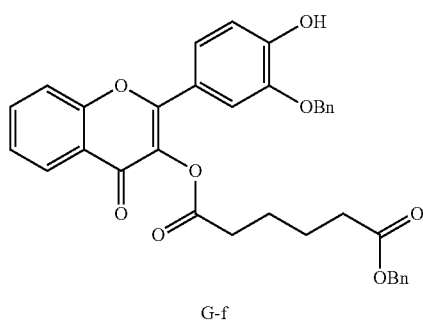

To a solution of intermediate G-e (11.7 g, 2.73 mmol) in dioxane (10 mL) was added a HCl/dioxane solution (5.75 M, 15 mL) and the mixture was stirred at RT for 10 min. The reaction was quenched by slow addition of a saturated aqueous $NaHCO_3$ solution and extracted with EtOAc (100 mL×2). The combined organic extracts were washed with brine, dried over $Na_2SO_4$, filtered and concentrated in vacuo. The residue was rinsed with a 25% EtOAc/Pet. Ether solution to give the product (1.30 g, 82%) as a yellow solid. TLC: $R_f$=0.45 (silica gel, Pet.ether/EtOAc=2/1, v/v); LCMS: m/z 579.2 [M+H]$^+$, 601.2 [M+Na]$^+$; $^1$HNMR: (400 MHz, DMSO-$d_6$) δ ppm 10.1 (br s, 1H), 8.07 (dd, J=7.8, 1.2 Hz, 1H), 7.89 (t, J=7.2 Hz, 1H), 7.79 (d, J=8.4 Hz, 1H), 7.57-7.52 (m, 4H), 7.47-7.32 (m, 9H), 7.03 (d, J=8.4 Hz, 1H), 5.21 (s, 2H), 5.10 (s, 2H), 2.60 (m, 2H), 2.42 (m, 2H), 1.65 (m, 4H).

Synthesis of G-g

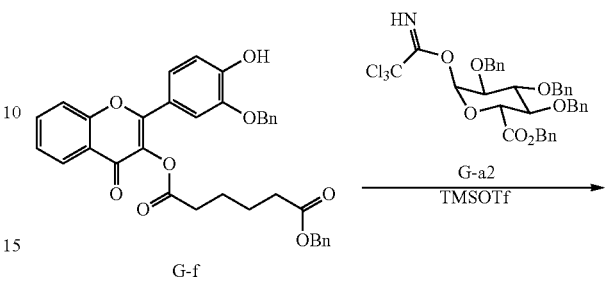

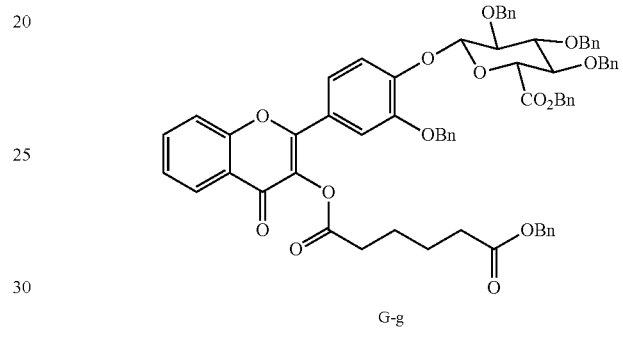

To a solution of intermediate G-f (240 mg, 0.41 mmol) in dry DCM (3 mL) under $N_2$ was added 4 Å molecular sieves (100 mg) and a solution of compound G-a2 (380 mg, 0.54 mmol) in DCM (1 mL). The mixture was stirred at RT for 5 min then cooled to −40° C. and a solution of TMSOTf (7 mg, 32.8 mol) in DCM (0.2 mL) was added dropwise. The mixture was then allowed to warm to RT and stirred overnight. The reaction was quenched by addition of TEA and the mixture was filtered. The filtrate was concentrated in vacuo and the residue was purified by preparative HPLC to give the product (100 mg, 22%) as a yellow solid. TLC: $R_f$=0.60 (silica gel, Pet.ether/EtOAc=2/1, v/v).

Synthesis of Glucuronide 1 (18)

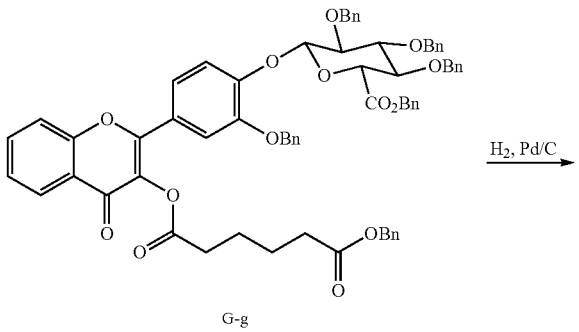

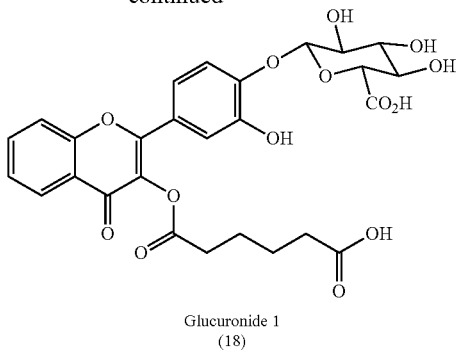

Glucuronide 1
(18)

A mixture of intermediate G-g (100 mg, 89.7 μmol) and 10% Pd/C (100 mg) was stirred at RT under a $H_2$ atmosphere (1 atm) overnight, TLC analysis (DCM/MeOH, 5/1, v/v) showed that the reaction was incomplete. The catalyst was removed by filtration, Pearlman's catalyst (100 mg) was added and the mixture was stirred at RT under a $H_2$ atmosphere (1 atm) for 2 h, TLC analysis (DCM/MeOH, 5/1, v/v) showed that the reaction was complete. The catalyst was removed by filtration and the filtrate was concentrated in vacuo. The residue was purified by preparative HPLC to give the product (10.8 mg, 21%) as a yellow solid. NMR analysis revealed a ~1:1.5 mixture of α and β-anomers. TLC: $R_f$=0.05 (silica gel, DCM/MeOH=5/1, v/v); LCMS: m/z 575.2 [M+H]$^+$, 597.2 [M+Na]$^+$; $^1$HNMR: (400 MHz, MeOD/DMSO-$d_6$) δ ppm 8.19 (d, J=7.6 Hz, 1H), 7.88 (m, 1H), 7.77 (d, J=7.6 Hz, 1H), 7.56 (t, J=7.6 Hz, 1H), 7.49-7.32 (m, 3H), 5.66 (d, J=3.2 Hz, 0.4H), 5.10 (d, J=7.2 Hz, 0.6H), 4.16 (d, J=10.0 Hz, 0.6H), 4.07 (d, J=9.6 Hz, 0.6H), 3.96 (t, J=9.2 Hz, 0.6H), 3.73-3.56 (m, 3.2H), 2.72 (t, J=9.2 Hz, 2H), 2.36 (t, J=9.2 Hz, 2H), 1.82-1.67 (m, 4H).

Synthesis of G2-a

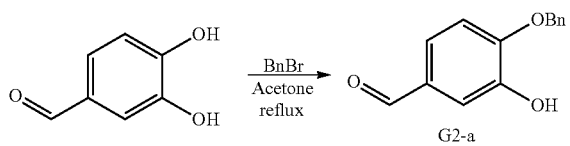

To a solution of 3,4-dihydroxybenzaldehyde (10.0 g, 72.4 mmol) and benzyl bromide (12.4 mmol, 72.4 mmol, 1.0 eq.) in acetone (400 mL) was added $K_2CO_3$ (15.0 g, 109 mmol) and KI (1.2 g, 7.14 mmol) and the mixture was heated at reflux for 5 h. The solid was removed by filtration and washed with EtOAc. The filtrate was concentrated in vacuo and the residue was purified by column chromatography (DCM/Pet. Ether, 0-100%, v/v) to give the product (9.2 g, 62%) as a white solid. TLC: $R_f$=0.65 (silica gel, Pet.ether/EtOAc=4/1, v/v); $^1$H NMR: (400 MHz, CDCl$_3$) δ ppm 9.83 (s, 1H), 7.42 (m, 7H), 7.03 (d, J=8.3 Hz, 1H), 6.00 (s, 1H), 5.20 (s, 2H).

Synthesis of G2-b

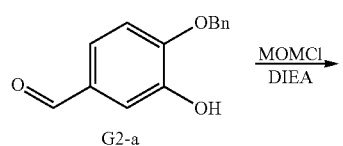

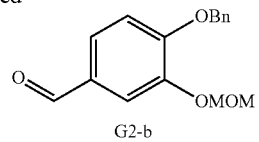

To a solution of intermediate G2-a (9.20 g, 40.3 mmol) in DCM (200 mL) was added DIPEA (10.4 g, 80.6 mmol) followed by MOMCl (4.87 g, 60.5 mmol) and the mixture stirred at RT overnight. The solvent was removed in vacuo and the residue was diluted with water and extracted with EtOAc (200 mL). The organic extract was washed with a 1 M aqueous HCl solution (×2), brine, dried over Na$_2$SO$_4$, filtered and concentrated in vacuo to give the product (10.0 g, 91%) as a yellow oil, which was used directly in the next step without further purification. TLC: $R_f$=0.60 (silica gel, Pet.ether/EtOAc=4/1, v/v); $^1$HNMR: (400 MHz, CDCl$_3$) δ ppm 9.85 (s, 1H), 7.69 (d, J=1.9 Hz, 1H), 7.51-7.35 (m, 6H), 7.04 (d, J=8.3 Hz, 1H), 5.30 (s, 2H), 5.26 (s, 2H), 3.54 (s, 3H).

Synthesis of G2-c

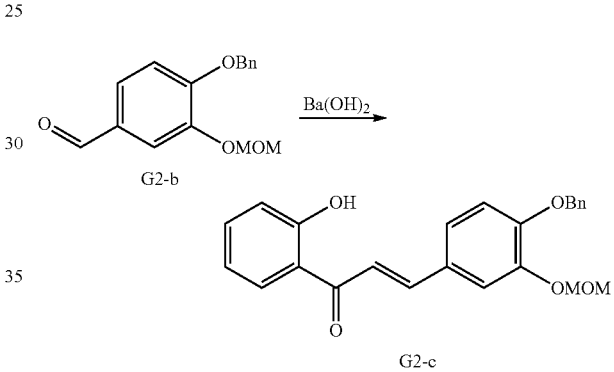

A mixture of intermediate G2-b (10.0 g, 36.7 mmol), 1-(2-hydroxyphenyl) ethanone (5.00 g, 36.7 mmol) and Ba(OH)$_2$ (12.6 g, 73.4 mmol) in MeOH (200 mL) was heated at 40° C. overnight. The mixture was diluted with EtOAc and the solid was collected by filtration. The filter cake was taken up in a dilute aqueous HCl solution and extracted with EtOAc. The combined organic extracts were washed with brine, dried over Na$_2$SO$_4$, filtered and concentrated in vacuo to give the product (12.4 g, 86%) as a yellow solid. TLC: $R_f$=0.70 (silica gel, Pet.ether/EtOAc=4/1, v/v); $^1$HNMR: (400 MHz, DMSO-$d_6$) δ ppm 12.7 (br s, 1H), 8.22 (dd, J=8.0, 1.2 Hz, 1H), 7.86 (AB, J=15.2 Hz, 1H), 7.77 (AB, J=15.6 Hz, 1H), 7.66 (d, J=1.9 Hz, 1H), 7.58-7.32 (m, 7H), 7.16 (d, J=8.5 Hz, 1H), 7.00 (m, 2H), 5.27 (s, 2H), 5.19 (s, 2H), 3.41 (s, 3H).

Synthesis of G2-d

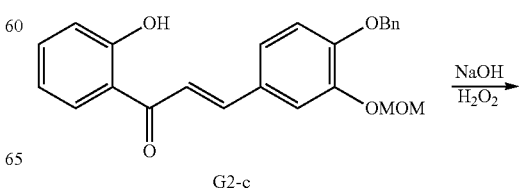

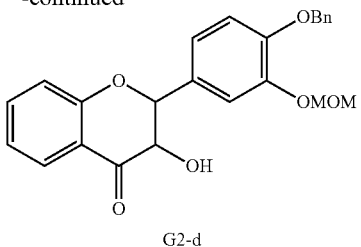

v/v) LCMS: m/z 623.3 [M+H]⁺, 645.2 [M+Na]⁺; ¹HNMR: (400 MHz, DMSO-d₆) δ ppm 8.09 (dd, J=8.0, 1.5 Hz, 1H), 7.86 (m, 1H), 7.78 (d, J=8.3 Hz, 1H), 7.70 (d, J=2.2 Hz, 1H), 7.62 (dd, J=8.6, 2.2 Hz, 1H), 7.52 (m, 3H), 7.42 (m, 2H), 7.33 (m, 7H), 5.26 (s, 2H), 5.23 (s, 2H), 5.10 (s, 2H), 3.43 (s, 3H), 2.67 (m, 2H), 2.42 (m, 2H), 1.67 (m, 4H).

Synthesis of G2-f

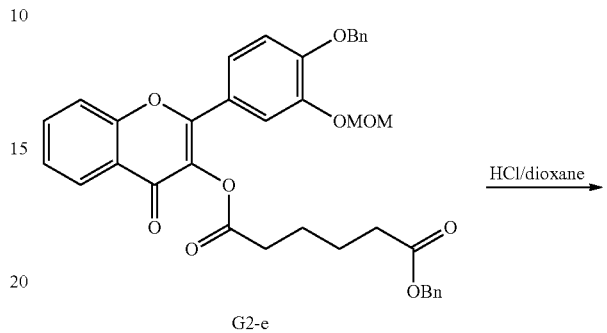

To a solution of intermediate G2-c (6.00 g, 15.4 mmol) in MeOH (100 mL) at 0° C. was added a 5.6% aqueous NaOH solution (49 mL) followed by H₂O₂ (30%, 5.7 mL) dropwise and the mixture was stirred at 0° C. for 2 h, then allowed to warm slowly to RT and stirred overnight. The mixture was poured into a dilute aqueous HCl solution and the solid was collected by filtration and washed with water, EtOH then dried in vacuo to give the product (4.90 g, 79%) as a yellow solid. TLC: R_f=0.43 (silica gel, Pet.ether/EtOAc=4/1, v/v); LCMS: m/z 405.1 [M+H]⁺, 427.1 [M+Na]⁺. ¹HNMR: (400 MHz, DMSO-d) □ ppm 9.50 (br s, 1H), 8.09 (d, J=8.0 Hz, 1H), 7.98 (s, 1H), 7.90 (d, J=8.8 Hz, 1H), 7.76 (m, 2H), 7.49-7.26 (m, 7H), 5.23 (s, 2H), 5.21 (s, 2H), 3.42 (s, 3H).

Synthesis of G2-e

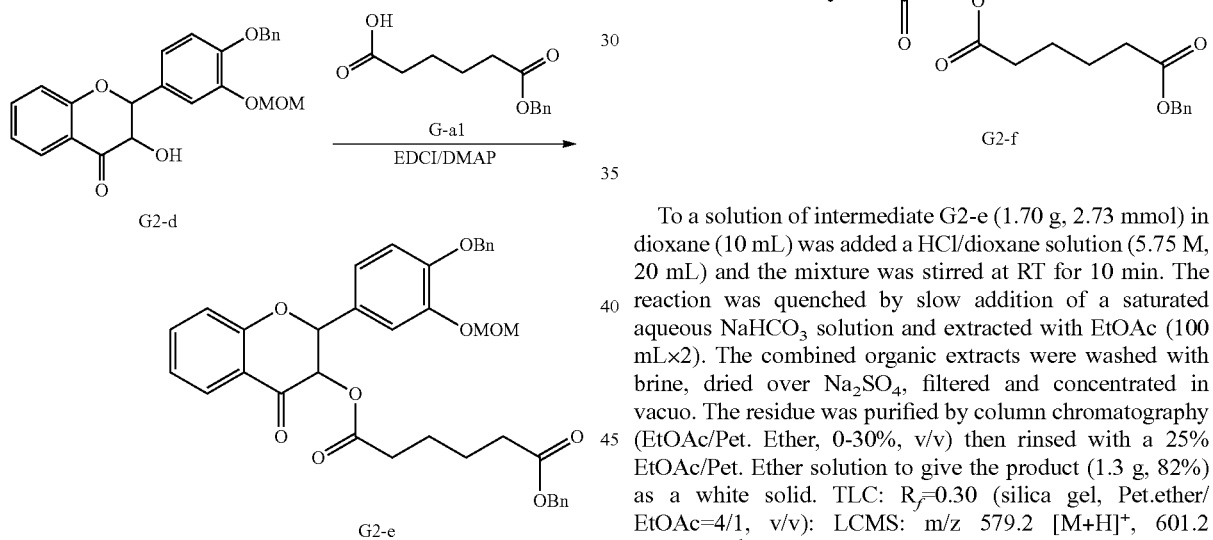

To a solution of intermediate G2-d (1.50 g, 3.71 mmol) and intermediate G-a1 (1.67 g, 7.05 mmol) in DCM (60 mL) was added EDCI (1.06 g, 5.56 mmol) followed by DMAP (0.45 g, 3.71 mmol) and the mixture was stirred at RT overnight, TLC analysis (Pet. Ether/EtOAc, 3/1, v/v) showed that some starting material remained. More EDCI (0.5 g, 2.61 mmol) and DMAP (0.2 g, 1.64 mmol) were added and stirring was continued for a further 1 h, TLC analysis (Pet. Ether/EtOAc, 3/1, v/v) showed that the starting material was consumed. The solvent was removed in vacuo and the residue was diluted with water and extracted with EtOAc (100 mL). The organic extract was washed with a 1 M aqueous HCl solution, a saturated aqueous Na₂CO₃ solution, brine, dried over Na₂SO₄, filtered and concentrated in vacuo. Purification by column chromatography (DCM/Pet. Ether, 0-100%, v/v) gave the product (1.70 g, 73%) as a yellow oil. TLC: R_f=0.40 (silica gel, Pet.ether/EtOAc=3/1, To a solution of intermediate G2-e (1.70 g, 2.73 mmol) in dioxane (10 mL) was added a HCl/dioxane solution (5.75 M, 20 mL) and the mixture was stirred at RT for 10 min. The reaction was quenched by slow addition of a saturated aqueous NaHCO₃ solution and extracted with EtOAc (100 mL×2). The combined organic extracts were washed with brine, dried over Na₂SO₄, filtered and concentrated in vacuo. The residue was purified by column chromatography (EtOAc/Pet. Ether, 0-30%, v/v) then rinsed with a 25% EtOAc/Pet. Ether solution to give the product (1.3 g, 82%) as a white solid. TLC: R_f=0.30 (silica gel, Pet.ether/EtOAc=4/1, v/v): LCMS: m/z 579.2 [M+H]⁺, 601.2 [M+Na]⁺; ¹HNMR: (400 MHz, DMSO-d₆) δ ppm 9.67 (br s, 1H), 8.08 (d, J=8.0 Hz, 1H), 7.87 (m, 1H), 7.78 (d, J=8.4 Hz, 1H), 7.56-7.32 (m, 13H), 7.20 (d, J=8.8 Hz, 1H), 5.22 (s, 2H), 5.11 (s, 2H), 2.67 (m, 2H), 2.42 (m, 2H), 1.67 (m, 4H).

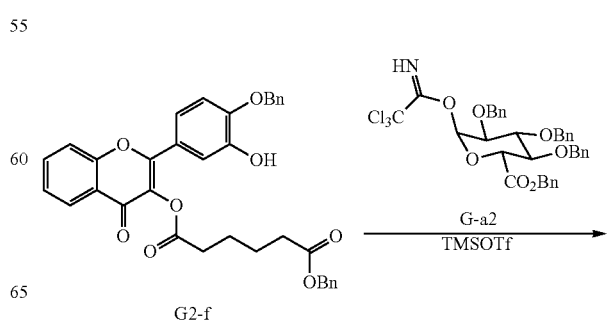

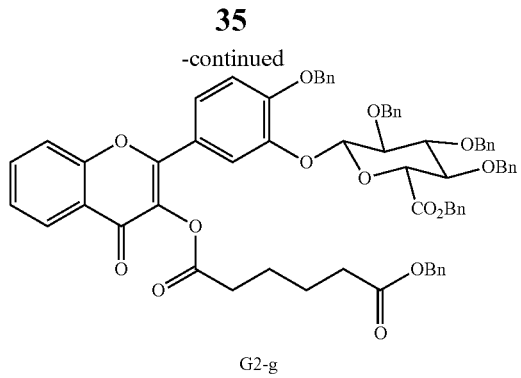

G2-g

To a solution of intermediate G2-f (200 mg, 0.35 mmol) in dry DCM (5 mL) under N₂ was added 4 Å molecular sieves (40 mg) and compound G-a2 (200 mg, 0.27 mmol). The mixture was stirred at RT for 5 min then cooled to −40° C. and a solution of TMSOTf (3 mg, 32.8 µmol) in DCM (0.2 mL) was added dropwise. The mixture was then allowed to warm to RT and stirred overnight. The reaction was quenched by addition of TEA and the mixture was filtered. The filtrate was concentrated in vacuo and the residue was purified by column chromatography (EtOAc/Pet. Ether, 0-25%, v/v) followed by preparative TLC (EtOAc/Pet. Ether, 50% v/v) to give the product (60 mg, 20%) as a colorless oil. NMR analysis revealed a ~1:1.5 mixture of α and β anomers. TLC: $R_f$=0.60 (silica gel, Pet.ether/EtOAc=2/1, v/v); ¹HNMR: (400 MHz, DMSO-$d_6$) δ ppm 8.08 (m, 1H), 7.90-7.65 (m, 4H), 7.54 (m, 1H), 7.48-7.41 (m, 2H), 7.36-7.07 (m, 29H), 6.03 (d, J=3.2 Hz, 0.4H), 5.55 (d, J=7.6 Hz, 0.6H), 5.33-4.97 (m, 7H), 4.87-4.66 (m, 4H), 4.60-4.42 (m, 2H), 4.09-3.68 (m, 3H), 2.68-2.56 (m, 2H), 2.38 (m, 2H), 1.61 (m, 4H).

Synthesis of Glucuronide 2 (17)

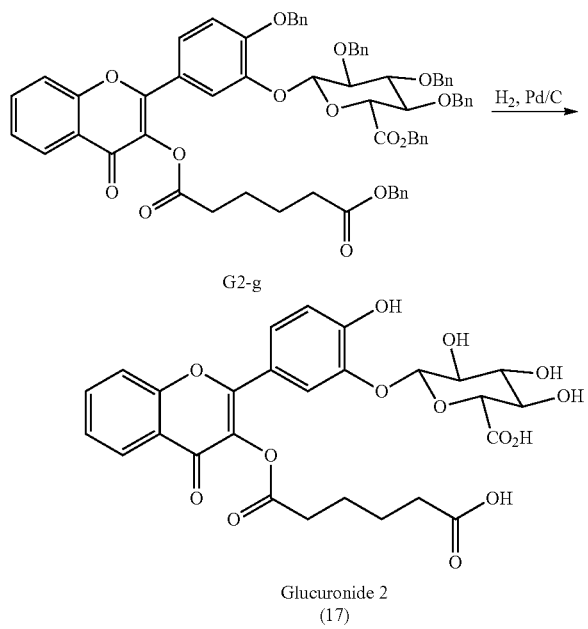

A mixture of intermediate G2-g (17 mg, 15.2 µmol) and 10% Pd/C (30 mg) was stirred at RT under a H₂ atmosphere (1 atm) overnight. The catalyst was removed by filtration and the filtrate was concentrated in vacuo. The residue was purified by preparative HPLC to give the product (1.0 mg, 11%) as a yellow solid. TLC: $R_f$=0.05 (silica gel, MeOH/DCM=1/5, v/v); LCMS: m/z 575.2 [M+H]⁺, 597.2 [M+Na]⁺.

Synthesis of Side Chain G-a1

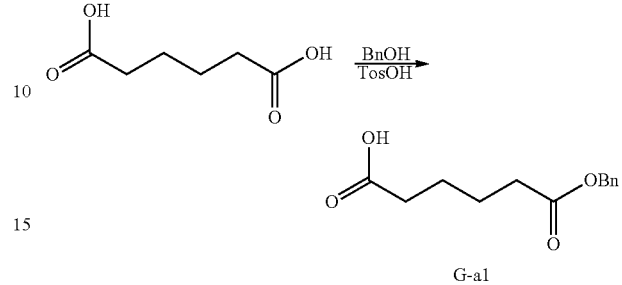

G-a1

A mixture of adipic acid (10.0 g, 68.4 mmol), BnOH (11.1 g, 100 mmol) and p-TsOH (129 mg, 0.68 mmol) in toluene (60 mL) was heated at reflux in a flask equipped with a Dean-Stark trap overnight. The mixture was cooled to RT, diluted with water and basified to pH>10 with a 6 M aqueous NaOH solution. The aqueous mixture was washed with EtOAc (100 mL×2), acidified to pH<4 with a dilute aqueous HCl solution and extracted with EtOAc (100 mL). The organic extract was washed with brine, dried over Na₂SO₄, filtered and concentrated in vacuo to give the product (5.4 g, 33%) as a colorless oil. TLC: $R_f$=0.2 (silica gel, Pet.ether/EtOAc=4/1, v/v); LCMS (negative mode): m/z 235.1 [M−H]⁻; ¹HNMR: (400 MHz, DMSO-$d_6$) δ ppm 7.31 (m, 5H), 5.07 (s, 2H), 2.34 (m, 2H), 2.20 (m, 2H), 1.52 (m, 4H).

Synthesis of Side Chain S1-a

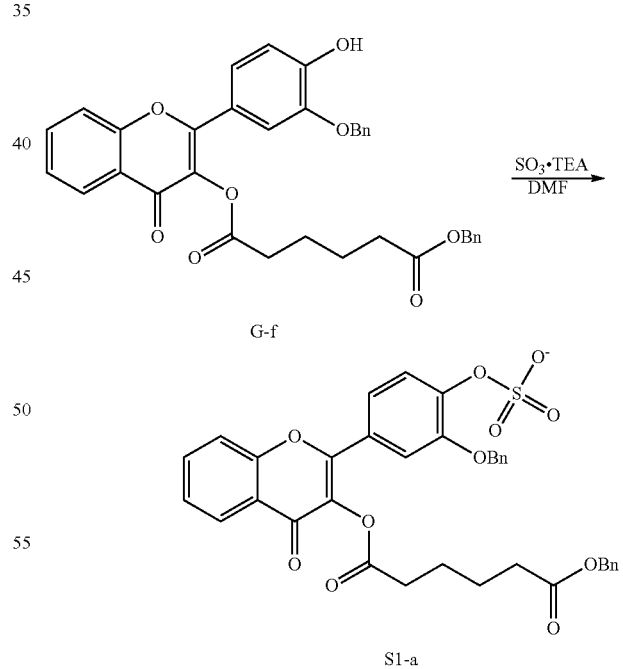

A mixture of intermediate G-f (115 mg, 0.20 mmol) and SO₃.TEA (181 mg, 1.00 mmol) in DMF (2 mL) was heated at 70° C. for 2 h then cooled to RT and poured into a solution of TEA (1 mL) in water (20 mL). The mixture was extracted with EtOAc (20 mL×2) and the combined organic extracts were washed with water (×3), dried over Na₂SO₄, filtered and concentrated in vacuo to a final volume of ~1 mL. The mixture was used directly in the next step. TLC: $R_f$=0.2 (silica gel, DCM/MeOH=10/1, v/v; LCMS (negative mode): m/z 657.5 [M–H]⁻.

Synthesis of Side Chain Sulfate 1 (57)

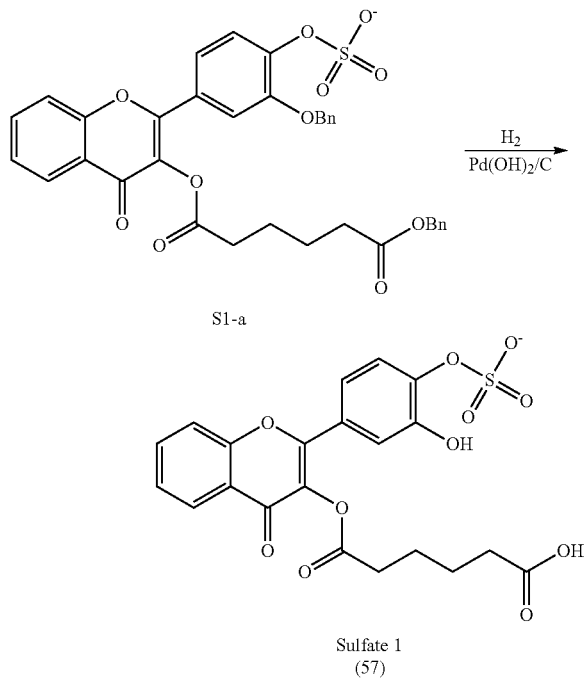 [SMILES: O=C(CCCCC(=O)Oc1c(-c2ccc(OS(=O)(=O)[O-])c(OCc3ccccc3)c2)oc2ccccc2c1=O)OCc1ccccc1 ; "H2" ; O=C(O)CCCCC(=O)Oc1c(-c2ccc(OS(=O)(=O)[O-])c(O)c2)oc2ccccc2c1=O]

S1-a

Sulfate 1
(57)

The EtOAc solution of intermediate S1-a (assumed 0.2 mmol) was diluted with EtOH (3 mL), Pearlman's catalyst (30 mg) was added and the mixture was stirred at RT under a H₂ atmosphere (1 atm) for 2 h. The catalyst was removed by filtration and the solvent was removed in vacuo. The residue was taken up in a saturated aqueous NaHCO₃ solution (1 mL), freeze-dried and re-dissolved in water (1 mL). The aqueous mixture was loaded onto an SPE column (C18, 8 g) and eluted with water, monitoring the fractions by HPLC. The product (17 mg, 27%) was obtained as a yellow solid after freeze-drying, NMR revealed the presence of ~0.6 equiv of TEA (counter-ion not shown). TLC: $R_f$=0.2 (silica gel, DCM/MeOH=5/1, v/v); LCMS (negative mode): m/z 477.4 [M–H]⁻; ¹HNMR: (400 MHz, MeOD) δ ppm 8.18 (dd, J=8.0, 1.2 Hz, 1H), 7.84 (m, 1H), 7.74 (d, J=8.4 Hz, 1H), 7.61-7.49 (m, 3H), 7.44 (dd, J=8.4, 2.0 Hz, 1H), 3.16 (q, J=7.2 Hz, 4H), 2.72 (t, J=6.8 Hz, 2H), 2.29 (t, J=6.4 Hz, 2H), 1.77 (m, 4H), 1.29 (t, J=7.2 Hz, 6H).

Synthesis of Side Chain S2-a

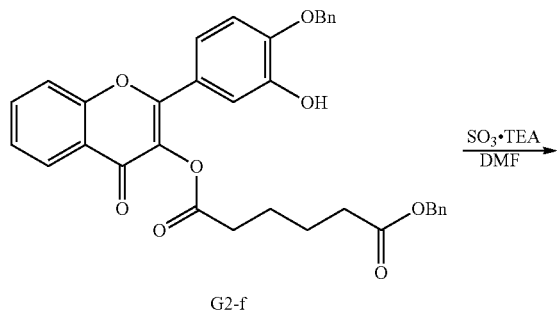

G2-f

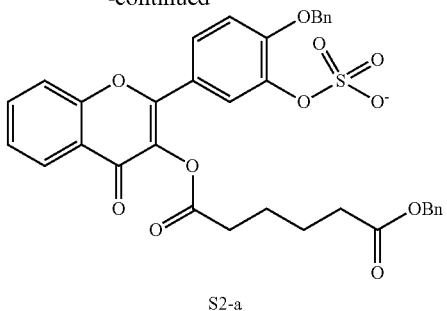

S2-a

A mixture of intermediate G2-f (115 mg, 0.20 mmol) and SO₃.TEA (181 mg, 1.00 mmol) in DMF (2 mL) was heated at 70° C. for 3 h, cooled to RT and poured into a solution of TEA (1 mL) in water (20 mL). The mixture was extracted with EtOAc (30 mL×2) and the combined organic extracts were washed with water (50 mL×4), brine, dried over Na₂SO₄, filtered and concentrated in vacuo to a final volume of ~2 mL. The mixture was used directly in next step. TLC: $R_f$=0.2 (silica gel, DCM/MeOH=10/1, v/v); LCMS (negative mode): m/z 657.5 [M–H]⁻.

Synthesis of Side Chain Sulfate 2 (56)

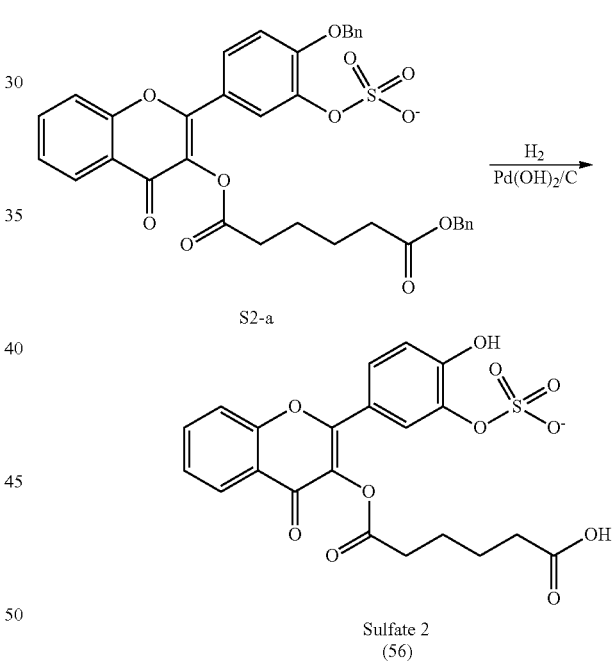

S2-a

Sulfate 2
(56)

The EtOAc solution of intermediate S2-a (assumed 0.20 mmol) was diluted with EtOH (20 mL), Pearlman's catalyst (50 mg) was added and the mixture was stirred at RT under a H₂ atmosphere (1 atm) for 3 h. The catalyst was removed by filtration and the solvent was removed in vacuo. The residue was taken up in a saturated aqueous NaHCO₃ solution (1 mL), freeze-dried and re-dissolved in water (1 mL). The aqueous mixture was loaded onto an SPE column (C18, 8 g) and eluted with water followed by 50% water/ MeCN, monitoring the fractions by HPLC. The product (50 mg, 52%) was obtained as a yellow solid after freeze-drying (counter-ion not shown). TLC: $R_f$=0.2 (silica gel, DCM/ MeOH=5/1, v/v); LCMS (negative mode): m/z 477.5 [M–H]⁻; ¹HNMR: (400 MHz, MeOD) δ 8.20-8.09 (m, 2H), 7.82 (m, 1H), 7.77-7.65 (m, 2H), 7.49 (t, J=7.2 Hz, 1H), 6.91 (d, J=8.8 Hz, 1H), 2.80 (t, J=7.2 Hz, 2H), 2.25 (t, J=7.2 Hz, 2H), 1.78 (m, 4H).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention claimed is:

1. A compound of the formula

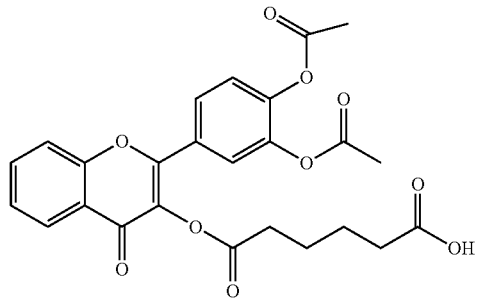 [SMILES: CC(=O)Oc1ccc(-c2oc3ccccc3c(=O)c2OC(=O)CCCCC(=O)O)cc1OC(C)=O]

or a pharmaceutically acceptable salt, hydrate, or solvate thereof.

* * * * *